United States Patent [19]

Gillio

[11] Patent Number: 5,791,908

[45] Date of Patent: Aug. 11, 1998

[54] APPARATUS AND METHOD FOR TELESURGERY

[76] Inventor: Robert G. Gillio, 2001 Pine Dr., Lancaster, Pa. 17601

[21] Appl. No.: 678,282

[22] Filed: Jul. 11, 1996

Related U.S. Application Data

[62] Division of Ser. No. 412,805, Mar. 29, 1995.

[51] Int. Cl.$^6$ .................................................. G09B 23/28
[52] U.S. Cl. ............................................................ 434/262
[58] Field of Search ....................................... 434/262, 263, 434/267, 270, 271, 272, 274, 275

[56] References Cited

U.S. PATENT DOCUMENTS

| | | | |
|---|---|---|---|
| 4,907,973 | 3/1990 | Hon | 434/262 |
| 5,130,794 | 7/1992 | Ritchey | 358/87 |
| 5,149,270 | 9/1992 | McKeown | 434/262 |
| 5,222,499 | 6/1993 | Allen et al. | 128/653.1 |
| 5,261,404 | 11/1993 | Mick et al. | 128/653.1 |
| 5,273,038 | 12/1993 | Beavin | 128/708 |
| 5,311,422 | 5/1994 | Loftin et al. | 364/401 |
| 5,343,871 | 9/1994 | Bittman et al. | 128/732 |
| 5,385,474 | 1/1995 | Brindle | 434/267 |

*Primary Examiner*—Richard J. Apley
*Assistant Examiner*—John Edmund Rovnak
*Attorney, Agent, or Firm*—Kenyon & Kenyon

[57] ABSTRACT

A virtual surgery system or virtual testing system provides a simulation or test based on image data. A simulator combined with a real exam requires simulation tasks by a test taker. Additionally, a surgical procedure may be simulated using image data of a patient in devices simulating the physical instruments a surgeon uses in performing the actual procedure, for example. The user input device, such as a mouse, three dimensional mouse, joystick, seven dimensional joystick, full size simulator, etc., can be used in a virtual simulation to move through the image data while the user looks at the data and interaction of the input device with the image data on a display screen. Force feedback can be provided based on physical constraint models (of the anatomy, for example), or based on edge and collision detection between the virtual scope or virtual tool used by the operator and walls or edges of the image data in the image space. The virtual simulator may be used as a teaching, training, testing, demonstration, or remote telesurgery device, for example.

18 Claims, 14 Drawing Sheets

APPARATUS AND METHOD FOR TELESURGERY

This is a divisional continuation of U.S. patent application Ser. No. 08/412,805 filed on Mar. 29, 1995.

BACKGROUND OF THE INVENTION

The present invention relates to a virtual surgery system in which a surgical procedure may be simulated using image data of a patient and devices simulating the physical instruments a surgeon would use in performing the actual surgical procedure.

Various prior art training devices and devices used in surgical applications are described as follows.

U.S. Pat. No. 5,149,270 issued on Sep. 22, 1992 to McKeown discloses an apparatus for practicing surgical endoscopic procedures. The McKeown patent relates to simulators that incorporate features to simulate visual and manipulation surgical conditions for training surgeons in surgical procedures such as laparoscopy and hysteroscopy. The apparatus has a cavity in which an object simulating a human organ is mounted for performing the practice procedure. The cavity is closeable to outside view or access, thus forcing the individual to use and manipulate the instruments under conditions that mimic real life operating and diagnostic conditions. U.S. Pat. No. 5,149,270 is incorporated herein by reference in its entirety.

U.S. Pat. No. 4,907,973 issued on Mar. 13, 1990 to Hon discloses a medical investigative system in which a person interacts with the system to interject information that is utilized by the system to establish non-restricted environmental modeling of the realities of surrogate conditions to be encountered with invasive or semi-invasive procedures. This is accomplished by video display of simulated internal conditions that appear life-like, as well as by display of monitor data including, for example, blood pressure, respiration, heart beat rate and the like. U.S. Pat. No. 4,907,973 is incorporated herein by reference in its entirety.

U.S. Pat. No. 5,273,038 issued on Dec. 28, 1993 to Beavin discloses a computer system receiving two dimensional slice data of a heart or other organ to be simulated in three dimensions. This three dimensional image data and chemical composition data of the heart or other organ are stored in the computer memory. Then a Voxel View or three dimensional volume rendering program forms images of the organ to be studied. Diagnostic data obtained from a patient with electrical measurement signals including an electrocardiogram, electro-myogram, electro-encephalogram, and other diagnostic measured electrical signals obtained from a patient are fed into the system and are placed in computer memory. Physiological data of the patient, including the strength, weakness, and other parameters of the organ is also considered diagnostic data and is supplied into the system. This data may be fed in black and white or in color to a device which shows the organ for visualization, operation simulation, or training. U.S. Pat. No. 5,273,038 is incorporated herein by reference in its entirety.

U.S. Pat. No. 5,222,499 issued on Jun. 29, 1993 to Allen et al. discloses a fiducial implant for the human body that is detectable by an imaging system. The placement of the fiducial implant into a portion of the anatomy of the human body allows for the recreation of a particular image slice of the portion of the anatomy taken by an imaging system with respect to a first time period, at subsequent imaging sessions and also with different scan modalities. This provides a doctor with the ability to accurately follow the progress of the portion of the anatomy of interest.

U.S. Pat. No. 5,385,474 issued on Jan. 31, 1995 to Brindle discloses a method for simulating anesthesiology and operating room conditions including the following six steps: displaying initial patient simulated vital sign information from a memory to signify an initial patient condition; randomly modifying the displayed patient vital sign information according to a script matrix in a manner analogous to that in which a patient's vital signs would be effected in the operating room by drugs or other external effects, thereby indicating a deteriorating condition; displaying user options; evaluating the timeliness and appropriateness of user input selections from the options in response to the changes in patient vital sign information to improve its initial state or deteriorate to a critical state in accordance with the successive script blocks in the script matrix depending upon the user's response and timeliness.

U.S. Pat. No. 5,261,404 issued on Nov. 16, 1993 to Mick et al. discloses a three-dimensional mammal anatomy imaging system and method which provide images of the internal anatomy of a mammal. U.S. Pat. No. 4,261,404 is incorporated herein by reference in its entirety.

U.S. Pat. No. 4,331,422 issued on May 10, 1994 to Loftin et al. discloses a training system for use in a wide variety of training tasks and environments. Artificial intelligence is used to provide computer-aided training.

U.S. Pat. No. 5,343,871 issued on Sep. 6, 1994 to Bittman et al. discloses a method and apparatus for mediating a biofeedback session with a human subject in which measurements of electrophysiological quantities are used to control a presentation to the subject of a series of prestored audio-visual sequences designed to induce a desired psychological state when viewed.

U.S. Pat. No. 5,130,794 issued on Jul. 14, 1992 to Ritchey discloses a panoramic image based virtual reality display system.

SUMMARY OF THE INVENTION

The present invention relates to a virtual surgery system simulator or virtual testing system simulator providing a simulation or test based on image data. The test simulator can include test authoring, test taking, assessment, training, demonstration, etc. The present invention also relates to a simulator combined with a real exam which can require simulation tasks by a test taker. In a virtual surgery embodiment of the present invention, a surgical procedure may be simulated using image data of a patient and devices simulating the physical instruments a surgeon would use in performing the actual procedure, for example. Image data is stored in the memory of the computer which corresponds to a portion of an anatomy in a three dimensional data set. A user input device such as a mouse, joy stick, full size simulator mock-up, etc. is used to move through the image data while the user looks at the image data on a display screen. A virtual surgery or other virtual implementation can be simulated based on the image data and the movement of the input device.

In embodiments of the present invention, force feedback may be provided based on a collision detection between the virtual scope or virtual tool used by the operator and walls or edges of the image data in the image space. Physical constraint models may be used for the force feedback. Alternatively, edge detection and collision software may be used to detect a collision between the virtual scope or tool and the walls or edges of the image data. Force feedback is then performed in response to the edge and collision detection using mechanical, electromechanical, pneumatic, hydraulic, etc. type devices. The present invention may also be used as a teaching, training, testing, demonstration, etc. device. Demonstrations may be provided to a user of the simulator before, during or after the simulation. The testing mode provides questions before, during and after the testing simulation and requests the user to perform specific tasks as well as using text questions. The task questions require the user to go through the virtual image data in a particular manner using the scope or other virtual tool device and can determine whether or not the test taker is correctly performing the operation. In the tutorial or teaching mode the present invention provides feedback to the user such as the quality of performance of the user or giving helpful hints to the user to perform the required tasks.

Virtual surgical operations can be performed according to an embodiment of the present invention using recorded expert simulations or real-time tutorials via a video or other data feed line. Telesurgery can be performed using a simulator according to the present invention in which a surgeon performs functions using a virtual mock-up of surgical instruments while a robot in a remote location performs the actual surgery based on the surgeon's movements relating to the virtual surgical devices. This implementation of telesurgery could also be used in other applications in which a simulator is implemented to perform specific tasks or actual remote tasks are performed using a simulator while a robotic device performs the actual task based on the simulated movements.

BRIEF DESCRIPTION OF THE DRAWINGS

Other features and advantages of the present invention will become apparent in view of the following description taken in conjunction with the attached drawings.

DETAILED DESCRIPTION

Figure 1:
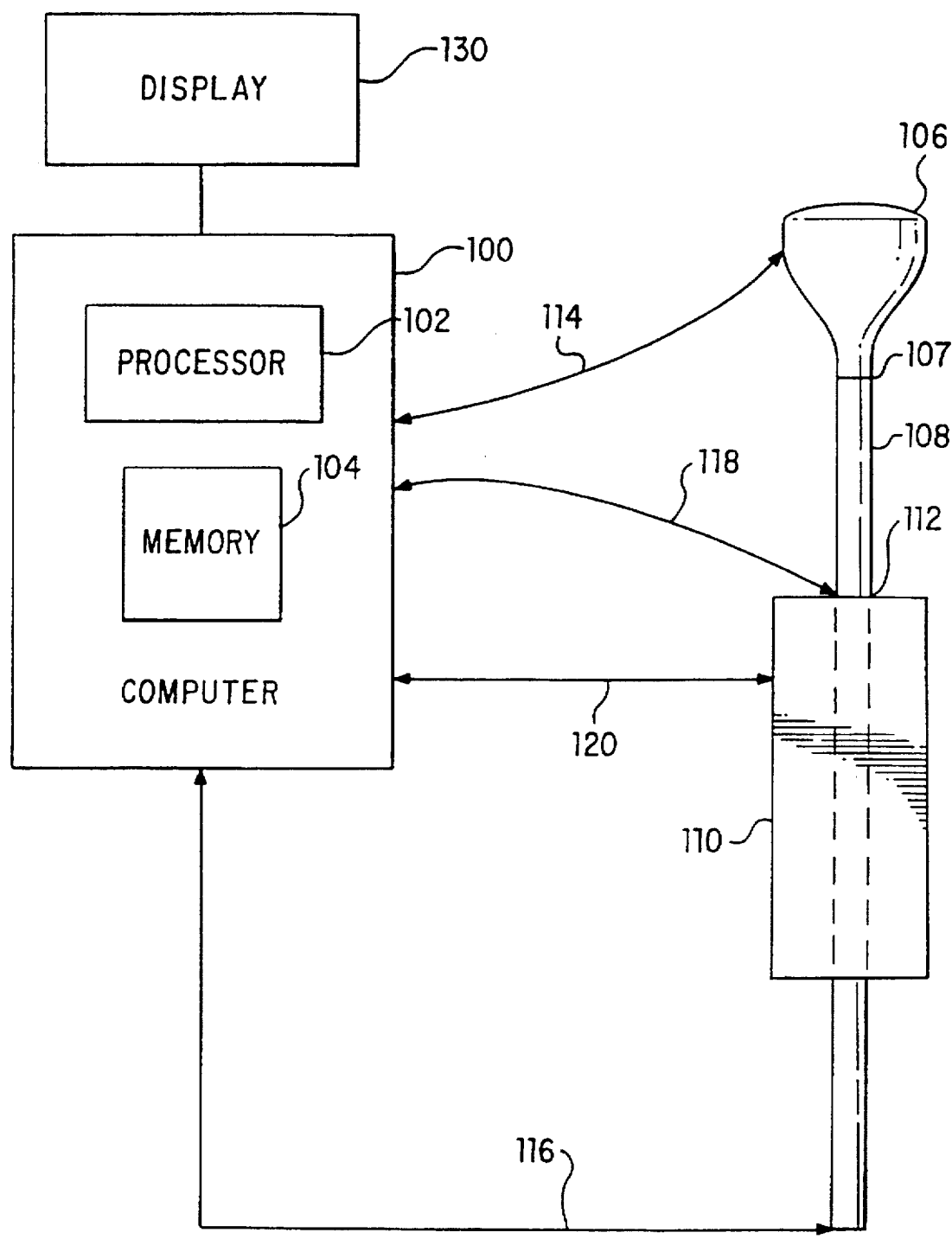
FIG. 1 illustrates a virtual surgery system according to an embodiment of the present invention.

FIG. 1 illustrates a virtual surgery system according to an embodiment of the present invention. The virtual surgery system includes a computer 100 including, for example, a processor 102 and a memory 104. The virtual surgery system additionally includes a virtual scope handle mouse device 106, a tube or endoscopic shaft 108 and a box device 110. The mouse device 106 corresponds to a real surgical instrument with a grabber, knife, laser, catheter, etc. on the working channel of the scope (or mouse). The tube 108 may be, for example, a tube, shaft, column, solid or hollow, flexible or stiff, with end deflection or no end deflection, and is inserted in a virtual orifice 112 of the box device 110. The virtual orifice may correspond to a mouth, nose, anus, or other orifice of the anatomy, or an incision in the anatomy. Feedback is provided from one or more of the mouse 106, the tube 108 and the virtual orifice 112 via lines 114, 116 and 118, respectively. Additionally, other feedback may be provided from the inside of box 110 to computer 100 via line 120. The computer can also control these various elements of the virtual surgery system using lines 114, 116, 118 and 120 (e.g., to implement force feedback, which will be described in further detail below). Further, the computer 100 is not necessarily dedicated only to the virtual surgery or other simulation. Computer 100 and/or processor 102 can also perform other functions or procedures in addition to the simulation described herein. That is, computer 100 can be a general purpose non-dedicated computer performing and/or able to perform a wide variety of tasks in addition to those corresponding to the virtual surgery simulation.

Image data is stored in memory 104 of the computer 100. This image data may be data corresponding to a portion of a human anatomy or an animal anatomy, or an entire human or animal anatomy. The image data stored in memory 104 may be a three dimensional data set obtained, for example, using image data using ultrasound techniques, or from a CT scan, a PET scan, an MRI scan, etc. Alternatively, the image data stored in memory 104 may be obtained using other various human anatomy image data (or other image data). For example, the National Library of Medicine provides image data of the entire human anatomy of a frozen cadaver which has been sliced, imaged and digitized. This visible human project image data is available through the National Library of Medicine, and may be obtained, for example, on the Internet at: ACKERMAN @ NLM.Gov.

Another example of a method of obtaining three-dimensional anatomy image data is provided in U.S. Pat. No. 5,261,404, which has been incorporated herein by reference.

Memory 104 may also store image data unrelated to or having no bearing on a human or animal anatomy. This image data may relate to particular volumes, shapes, sizes, textures, etc. This unrelated image data may be used in a virtual simulation where a user is learning how to use the scope prior to performing any virtual surgery simulations as described herein. This simulation is similar to a virtual surgery simulation, but operates on the unrelated image data.

In implementing a virtual surgical procedure, a mouse device 106 corresponding to the particular surgical procedure to be implemented with a virtual surgery system is attached to the tube 108 at point 107. A variety of mouse devices 106 may be attached at point 107 to allow a variety of surgical procedures using the virtual surgery system. Image data of, for example, the generic human anatomy or data corresponding to a particular patient are then retrieved from memory 104 and displayed on display device 130. Memory 104 stores data including, for example, a data set library of abnormalities, infections, etc. The data set library of abnormalities, infections, etc. may be related to a particular patient or medical information in general, such as tumors, infections, scans, Xrays, etc. For example, the data in memory 104 could include image data corresponding to a patient having bronchitis, a variety of tumors, or other conditions, foreign objects, etc. (either normal or abnormal).

The particular patient image data can be chosen by the surgeon prior to the virtual surgery operation by an input device connected to computer 100. For example, a keyboard device (not illustrated in FIG. 1) can be attached to computer 100 to allow a user to choose a particular operation to be performed or particular image data to be used in the virtual surgery procedure. Alternatively, the user can make the choice using other devices such as a touch screen on the display 130 or using a mouse device to choose a particular operation or image data currently displayed on the display 130. The surgeon is then able to do a "practice run" on a particular patient using the virtual surgery system prior to the actual surgery of the patient, for example. The virtual scope including the mouse device 106 and the endoscopic hose 108 can be used to navigate through a three dimensional image model. Further details and embodiments of the system illustrated in FIG. 1 and other virtual surgery system embodiments will be discussed below in reference to other detailed drawings of embodiments of the present invention. The virtual surgery system according to the present invention device can access an image data set of the anatomy to traverse, surgery to perform, etc. and can interpret the input device as that from a variety of different surgical instruments.

A summary of a patient's case, including history, physical exam, lab and Xray, vital signs and any other clinical data, for example, may also be stored in memory 104, displayed on display 130 simultaneously with a simulation being displayed on display 130, either before, during or after the surgery simulation. This data may be displayed on a split portion of the display, or in a small window portion of the display, etc. If the simulator is used in conjunction with a real surgery, that data can also be stored and/or displayed in addition to the simulation, before, during, or after the actual procedure or simulation. The image data and other clinical data corresponding to a patient can also be stored on a computer disk, for example, and placed in a patient's medical record for later use or review, if necessary.

Figure 2:
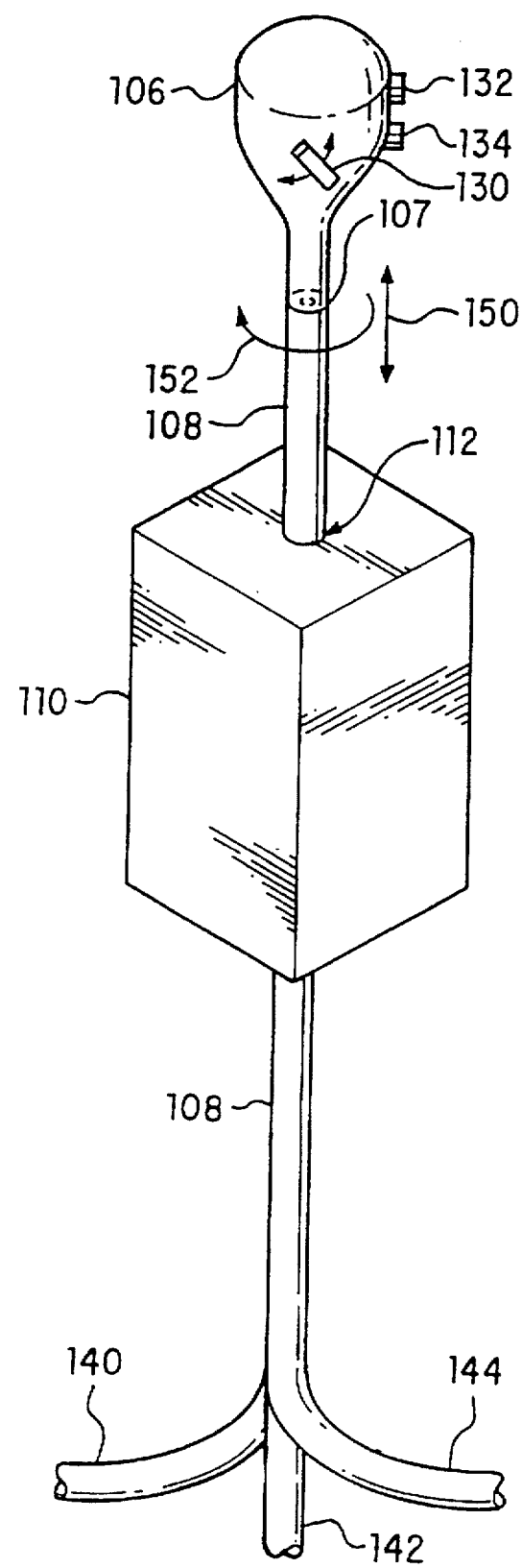
FIG. 2 illustrates a virtual mouse and virtual orifice and box connection which may be used in an embodiment of the present invention.

FIG. 2 illustrates a virtual mouse and virtual orifice and box connection which may be used according to an embodiment of the present invention. For example, the mouse, box and virtual orifice connection illustrated in FIG. 2 may be used in the overall virtual surgery system of FIG. 1. The same reference numerals as those of FIG. 1 are used in FIG. 2 to illustrate the same features of the present invention.

The virtual mouse 106 of FIG. 2 includes, for example, switches (or buttons, handles, etc.) 130, 132 and 134. These switches can perform various functions based on the endoscopic mouse or virtual scope being used to implement a particular surgery. For example, switch 130 may be used as an anterior-posterior end deflector which actually deflects the end of the tube 108 in a direction 140, 142, 144 according to the position of the switch 130 on the virtual mouse device or give information to the computer simulating such movement in a real surgical instrument either hand-held or robotic in a telesurgical operation. Switches 132 and 134 can be used, for example, for suction or air insufflation. The tube 108 may be a generic tube which can be rigid or flexible. Arrows 150 and 152 illustrate directions in which the virtual mouse scope 106 and hose 108 may be moved by a surgeon in performing virtual surgery. Arrow 150 illustrates that the mouse 106 and hose 108 may be moved in an up and down direction, while arrow 152 illustrates that the mouse and hose may be moved in a twisting or rotating motion. The mouse 106 and hose 108 could also be moved in x, y and z directions as well as pitch, roll, yaw and the rotating (or twisting) direction. Although the bottom of hose 108 is illustrated as being bent or bendable (or deflectable) in the embodiment of FIG. 2, other embodiments of the present invention can be implemented in which the bottom of hose 108 is not bent bondable deflected or deflectable. For example, an embodiment of the present invention may be used in which the hose is a straight tube used as an optical endoscope with no bending or deflection of the end of the tube.

Figure 3A:
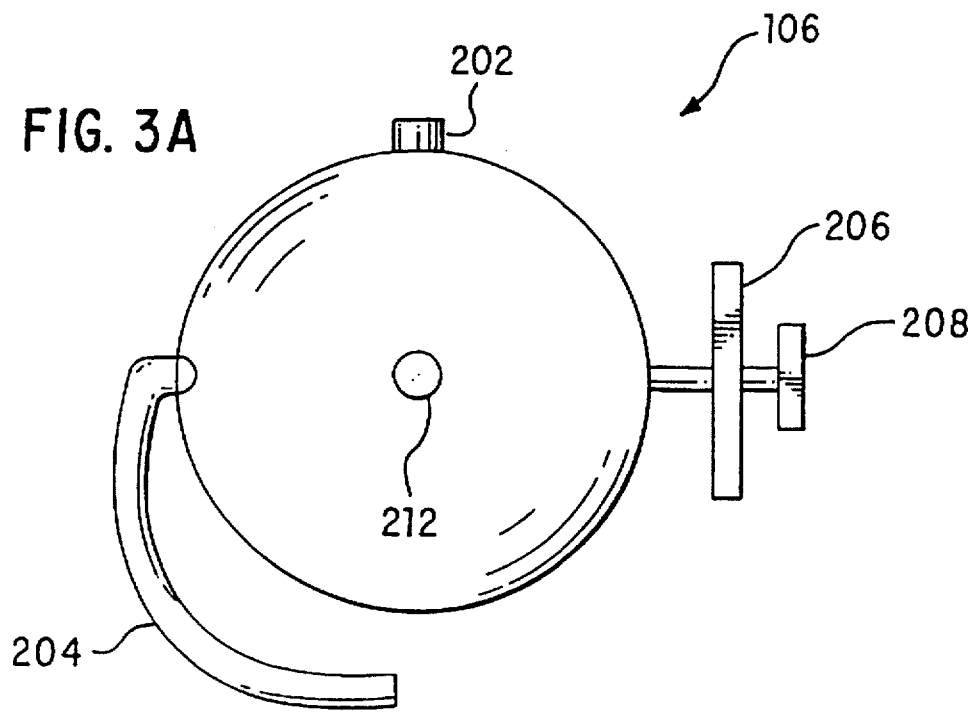
FIG. 3A illustrates a top view of a virtual mouse according to an embodiment of the present invention.
Figure 3B:
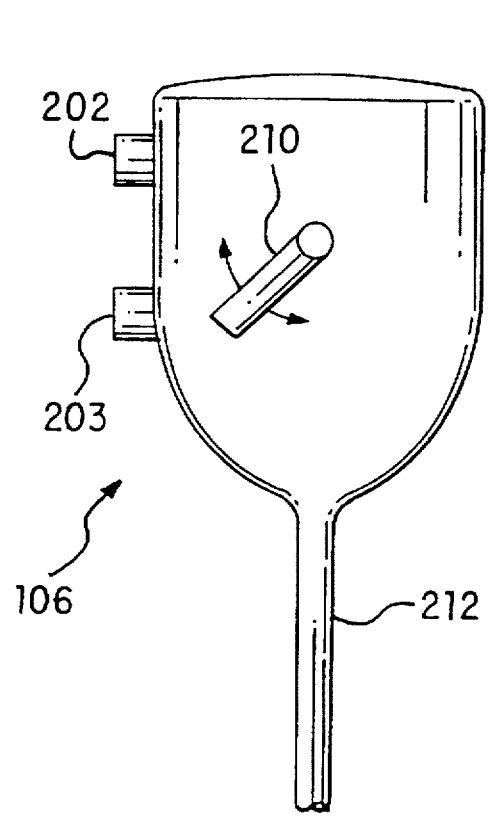
FIG. 3B illustrates a left side view of a virtual mouse according to an embodiment of the present invention.
Figure 3C:
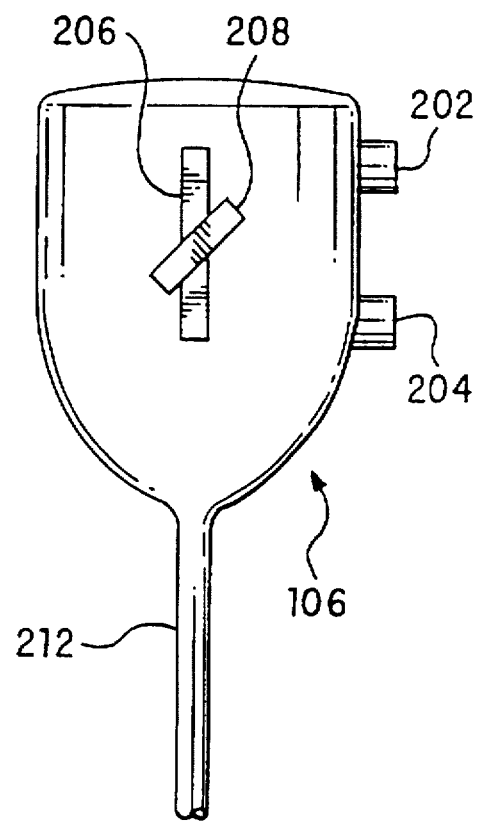
FIG. 3C illustrates a right side view of a virtual mouse according to an embodiment of the present invention.

A mouse device 106 which may be used in implementing the present invention and attached to a virtual surgery system similar to the mouse 106 in FIG. 1 and FIG. 2 is illustrated in FIG. 3A, FIG. 3B and FIG. 3C. FIG. 3A illustrates a top view of the endoscopic mouse 106, FIG. 3B illustrates a left side view thereof, and FIG. 3C illustrates a right side view. The mouse 106 includes switches 202, 203, 204, 206, 208 and 210. The mouse 106 illustrated in FIGS. 3A, 3B and 3C is an endoscopic mouse/virtual scope to be used in a bronchoscopy (using, for example, switch 204) or gastroscopy (using switches 206 and/or 208) type of operation. Switch 202 provides suction, switch 204 provides air insufflation, switch 206 is an anterior-posterior deflector, switch 208 is a lateral deflector and switch 210 is an anterior-posterior end deflector. Flexible shaft 212 of the mouse 106 is the flexible shaft portion which connects to the hose 108 at point 107. A variety of devices 106 could be placed at the end 107 of the hose 108 to model all sorts of surgical instruments or even tools used in other trades. That is, the present invention need not be limited to virtual surgery applications. For example, the virtual system of the present invention may be implemented in an industrial tool environment such as using a drill press, or in landscape architecture, building architecture, manufacturing, plumbing applications, sewage clearing, disasters in nuclear plants, jet or automobile engines, outer space applications, robotic devices, etc. This is advantageous in a virtual device in which a particular tool was attached to the hose 108 to simulate a particular procedure in which an instrument is attached to a tube-like hose such as hose 108 which is inserted into some other structure to perform a particular procedure.

Figure 4:
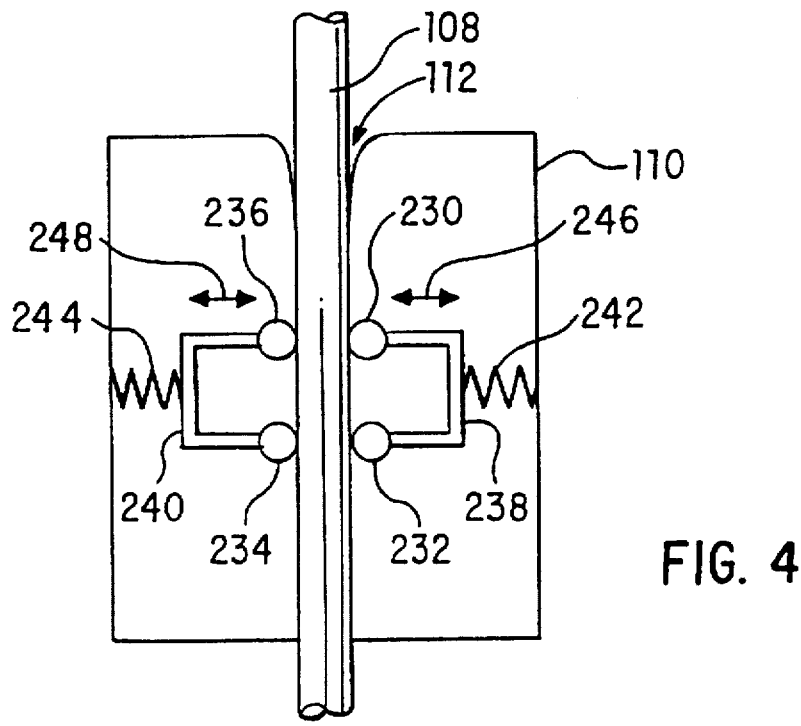
FIG. 4 illustrates a portion of a box device near a virtual orifice used to accommodate various inputs such as a hose used for virtual surgery.

FIG. 4 illustrates a portion of the box device 110 near the virtual orifice 112 which is used to accommodate various inputs such as the hose 108 used for virtual surgery. The virtual orifice 112 can accommodate various sizes of inputs and various inputs such as a rigid scope hose, a flexible scope hose or other tube-shaped devices. The tube 108 accommodated by the box 110 can correspond to various actual medical devices such as any endoscope, endotracheal tube, nasogastic tube, IV's, catheters, etc. The tube 108 is accommodated within the box 110 via rollers 230, 232, 234 and 236, arms 238 and 240, and springs 242 and 244. The arrangement of rollers 230, 232, 234 and 236, arms 238 and 240 and springs 242 and 246 moves in the direction of arrows 246 and 248 based on the size of the tube 108 being accommodated within the virtual orifice 112 and box 110. Additionally, the arrangement can be moved in this direction to provide force feedback to the hose. Spring tension can be increased by way of a solenoid pinching pressure on the rollers. One or more of the rollers 230, 232, 234 and 236 can also be fitted with stepper motors or friction devices to allow application of force. The computer (not shown in FIG. 4) can also be programmed to provide force as determined by the parameter being simulated, and a computer detection of resistance to movement or an encountering of a collision between, for example, the hose (or virtual scope device) with a virtual structure which is firm or has elastic properties.

Figure 5:
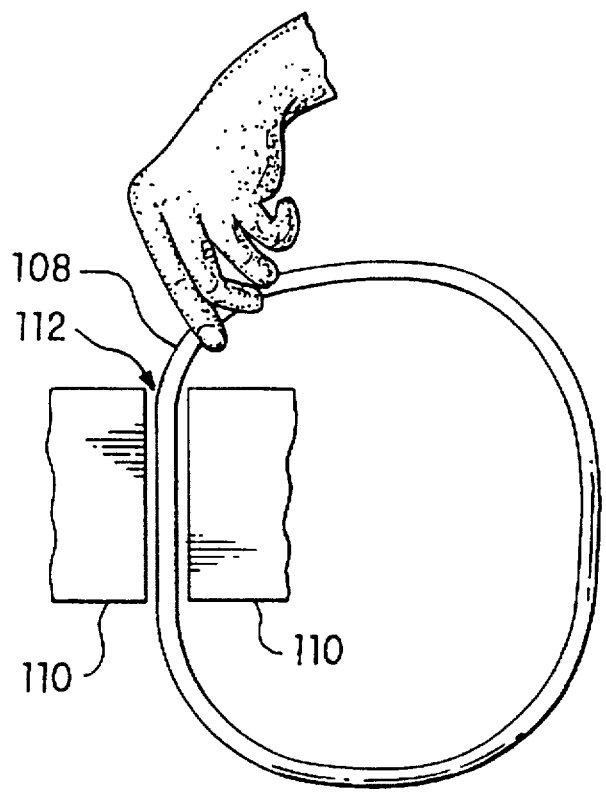
FIG. 5 illustrates an embodiment of the present invention in which a loop of flexible hose is accommodated within a box for instructional purposes.

FIG. 5 illustrates an embodiment of the present invention which uses a loop of flexible hose 108 which is accommodated within the box 110. The user of the virtual system can feed the hose 108 through the box 110 in an up and down or rotating, etc. manner similar to that described above. The hose may be pushed into or pulled out of the box 110, twisted, rotated, etc. This embodiment may be used as a training device for feeding a surgical hose through a virtual orifice 112. The virtual orifice may be adjusted (e.g., by computer programming or physical adjustment) to be any orifice of the body (e.g., mouth, nose, anus, etc.) or a puncture through the skin into a blood vessel. The additional corresponding anatomy would then follow. For example, when dedicated as the mouth, the anatomy encountered would be the adjacent structures such as the pharynx, larynx, esophagus, then stomach, etc.

Figure 6:
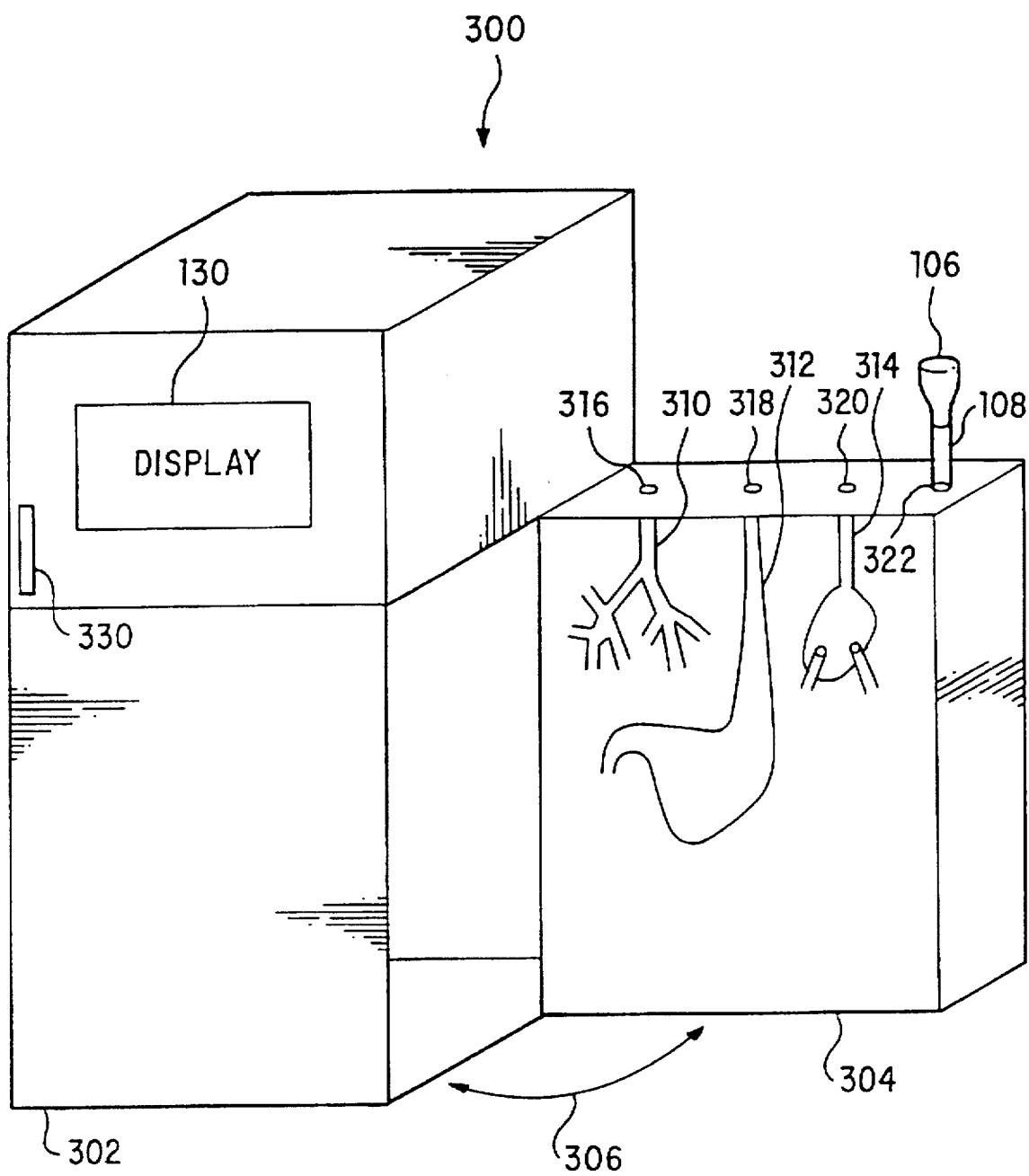
FIG. 6 illustrates a virtual reality surgical simulator which may be used in a kiosk form and which includes physical constraint models.

Tactile feedback may be provided to a mouse device such as an endoscopic simulator by attaching physical constraining models in which an input device is manipulated. As an example, the physical constraining model may be a portion of the bronchial anatomy, the gastrointestinal anatomy, urologic, or other portions of the anatomy such as walls of a blood vessel. The physical model constraints are constructed to be approximately the same size as the virtual computer model corresponding to image data stored in the memory of the computer. The physical constraining models may be used to provide tactile feedback as the hose (or endoscopic device) hits the physical walls of the physical model and the image walls on the computer image. This is an inexpensive way of providing tactile feedback without acquiring edge detection or collision detection software programs to determine when the mouse device or hose meets or collides with an edge or wall in the image data. Additionally, this method provides force feedback without any expensive stepper motors, magnets or other constraining devices required in the mouse device itself. FIG. 6 illustrates such a typical model constraint device in which virtual orifices are used through which a scope is traversed in a virtual surgery simulation. The scope is positioned over an appropriate physical constraint model for purposes of simulation so that the simulator can perform a variety of different types of surgical simulations.

FIG. 6 illustrates a virtual reality surgical simulator which may be provided in a kiosk form. The kiosk 300 includes a housing 302 which contains the computer 100 (not illustrated in FIG. 6) and the display 130. The kiosk 300 includes a side door 304 which can open as shown by arrows 306. Alternatively, door 304 could be a sliding door which slides straight out from the side of the housing 302. The door 304 is a large box-like structure which includes physical constraint models 310, 312 and 314. The physical constraint models used in this embodiment can each be a set of connecting tubular structure each representing a different portion of the internal anatomy. These physical constraint models can correspond to, for example, the lungs, the stomach, or the urologic portions of the anatomy, etc. Virtual orifices 316, 318, 320 and 322 are provided at the top portion of the door 304 of the kiosk 300. Alternatively, the virtual orifices could slide over the appropriate constraining model and snap into place with a physical latch and/or electrical connection with the computer to identify which portion of the anatomy is to be simulated. The virtual mouse 106 and hose 108 may be inserted through one of the virtual orifices 316, 318, 320 and 322 so that the endoscopic hose 108 is accommodated within the physical constraint models 310, 312, 314, etc. The physical constraint models can include any types of physical constraints corresponding to a portion of the anatomy which is to be surgically probed.

The physical constraint models 310, 312, 314 can be built as a physical model corresponding to different portions of the anatomy. The physical constraint models may be constructed using stereo lithography by taking a three-dimensional data model and shining lasers to heat a plastic plasma surface and provide a complex cast of the particular portion of the anatomy based on a physical computer model constructed from three-dimensional image data, as well as by more conventional means of modelling. When the surgical instrument (e.g., the hose 108) hits a wall of the physical constraint model 310, 312, 314, a device such as a magnet, actuator, solenoid, spring, etc. is used by the feedback system of the computer to provide force feedback. The force feedback device is connected via lines 114, 116, 118 and 120 of FIG. 1, for example, between the physical constraint model and the computer 100.

The kiosk 300 can also include a credit/access card swipe portion 330 which may be used to access the device using a magnetic card or a credit card to charge a user for use of the kiosk or virtual surgery system.

Other embodiments of the kiosk 300 of FIG. 6 could be implemented according to the present invention. For example, an embodiment could include a scope 106 separate from the simulator kiosk 300. In such an embodiment, a user walks up to the kiosk and plugs in his/her personal scope or scopes, for example. In another embodiment, a communication link to the simulator such as a telephone or satellite link may be used in combination with a virtual scope, joystick, etc. in a remote location. A demonstration (or simulation) can thus be performed on the display of the kiosk from a remote location. Alternatively, a remote home computer can be used at which the user moves the virtual scope or joystick, etc., and uses the processing power of a powerful computer such as an IBM mainframe computer, for example.

FIG. 6 illustrates a kiosk including a door device having a plurality of virtual orifices at the top. Alternative embodiments of the present invention include a box device permanently, temporarily, removably, exchangeably or detachably attached to a floor, wall, or table and having one or a plurality of virtual orifices therein A portable box which is removably attached to a table, wall, or floor, or not attached at all, may also be used in implementing embodiments of the present invention.

In an embodiment of the present invention in which a virtual simulation is used in a testing environment, a signature pad or other device for identifying a test taker can be used to identify the test taker.

While FIG. 6 illustrates an embodiment of the present invention in which physical constraint models are used to detect a physical actuation of a device against an edge of the physical constraint model, other methods may be used to detect the edge of the virtual scope hitting an edge of a virtual anatomy. For example, if physical constraint models are not used within the box 110, virtual models may be used by implementing known edge collision and detection software, such as the Telios program available from High Techsplantations of Bethesda, Md. or Engineering Animation, Inc. (EAI) of Ames, Iowa. Force feedback may then be provided from the edge collision and detection software running in the computer based on the image data to a force feedback device (e.g., magnet, solenoid, actuator, spring, etc.).

FIG. 7, FIGS. 8A and 8B, FIG. 9A and FIG. 9B illustrate a "joystick" or other desktop input device for a computer for a virtual reality simulation device. Alternatively, the "joystick" can be used in playing, for example, realistic three-dimensional video or computer games.

Figure 7:
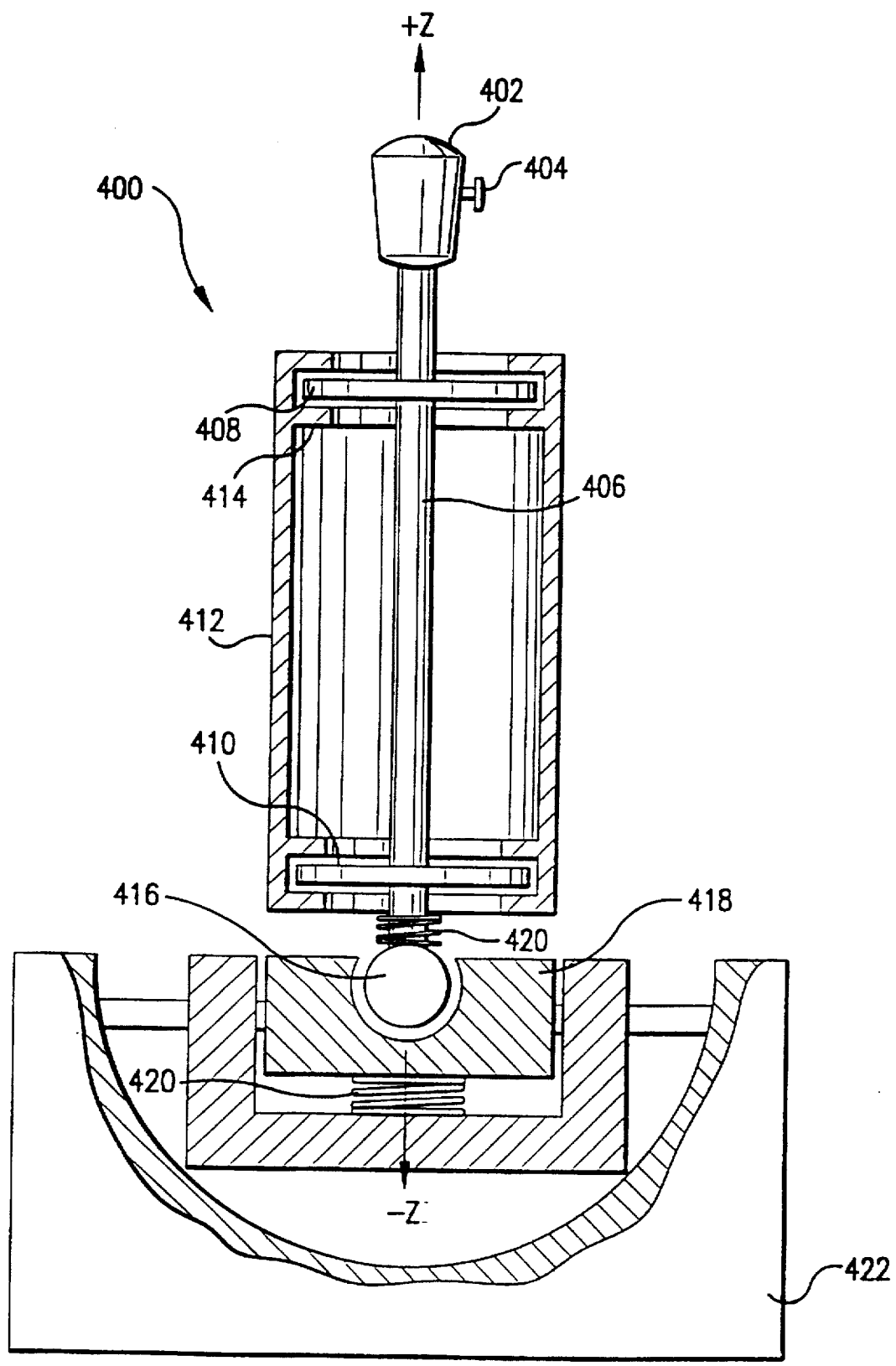
FIG. 7 illustrates a joystick having seven degrees of freedom for an inexpensive implementation of surgical (or other) simulation.
Figure 8B:
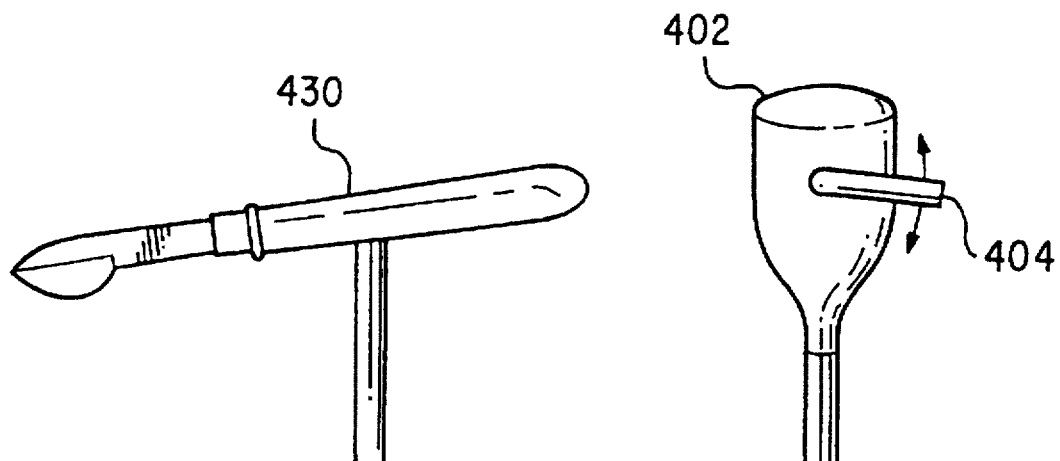
FIGS. 8A and 8B illustrate a further embodiment of a joystick according to the embodiment of FIG. 7.
Figure 8A:
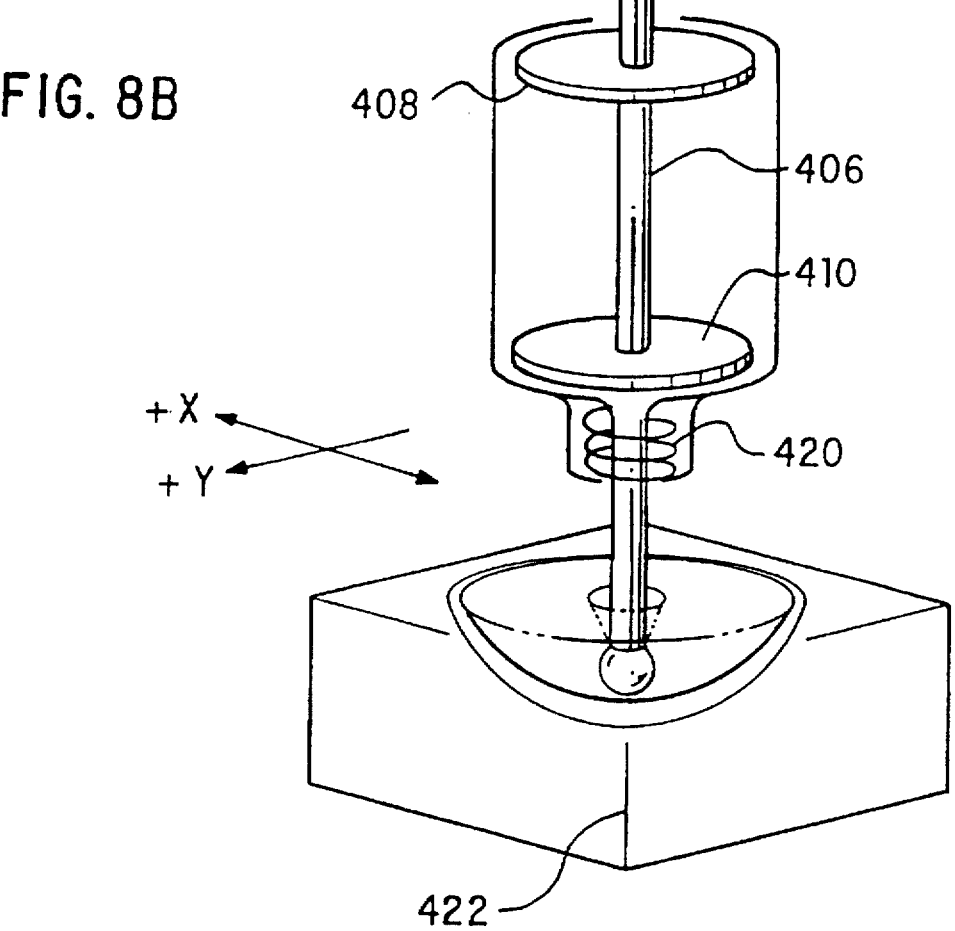

In the joystick illustrated in FIG. 7 and FIG. 8A and 8B, a shaft on a plunger is mounted inside an axle-like device which can be rotated and which is mounted in the frame in a pivotable manner. The joystick allows left and right, up and down, in and out, or x, y, z orientation, and allows inputs in a positive and negative direction for each variable. The handle of the joystick device may include switches or devices where the thumb and fingers grip the device for additional input from the user. A harness which holds the axle holding the piston can be mounted on a rotation device so that the rotation of the entire structure can be added as another coordinate of input movement (i.e., the rotational direction). The "joystick" or universal input device can be used as a three-dimensional mouse or to simulate a virtual surgery operation such as surgical an operation requiring endoscopic instrument positions.

FIG. 7 illustrates a joystick having seven degrees of freedom for an inexpensive implementation of surgical (or other) simulation. In using the joystick of FIG. 7, a surgical simulator may be provided which does not require the large kiosk illustrated in FIG. 6 and which can be implemented in, for example, a computer or video game implementation. Even if the joystick of FIG. 7 is not used in a computer game implementation, it may be used for other virtual surgery implementations. The joystick may also be used for other simulation implementations or general computer games which include seven degrees of freedom as illustrated in FIG. 7. Specifically, most joysticks have previously allowed movement in two directions (i.e., the x and y-directions). The joystick illustrated in FIG. 7 allows one to use a joystick having a better virtual movement in three dimensions. Specifically, the joystick of FIG. 7 allows movement in the x, y, z, pitch, roll, yaw and rotation directions.

Joystick 400 of FIG. 7 includes a handle having attached switches or dials 404. The shaft 406 allows movement in the plus/minus Z directions as illustrated by the arrow at the top of FIG. 7. Disks 408 and 410, which are attached to the top and bottom of shaft 406, respectively, provide a stabilization when the handle 402 is moved in a rotating or circular direction. Walls 400 of the joystick 400 include protrusions 414 which act in cooperation with disks 408 and 410 to maintain the joystick in a stable position upon the rotation thereof. Additionally, walls 412 and protrusions 414 may be used to measure the rotation of disks 408 and 410 to determine the amount of rotation in the joystick and provide electrical signals to the computer 100 relating to the rotation. The universal ball joint 416 allows a pivoting motion in the holder 418 to allow for movement in the x and y directions. Spring 420 allows up and down movement in the Z direction by allowing the vertical movement of the handle. A spherical base 422 allows pitch, roll and yaw of the joystick device.

A further embodiment of the joystick device according to the present invention is illustrated in FIGS. 8A and 8B. Electrical signals are fed back from different portions of the joystick such as the mouse handle 402, the disks 408 and 410, the spring 420, etc. Strain gages, spring deflectors and other devices used to measure the quantities and the signals are sent to the computer using electric wires or infrared radio frequency or other technology. The joystick is mechanically returned to a neutral position after being moved by a user when force is no longer provided to the handle by the user. Handle 402 can be detachably replaced by other handles such as scalpel 430 as shown in FIG. 8B.

Figure 9A:
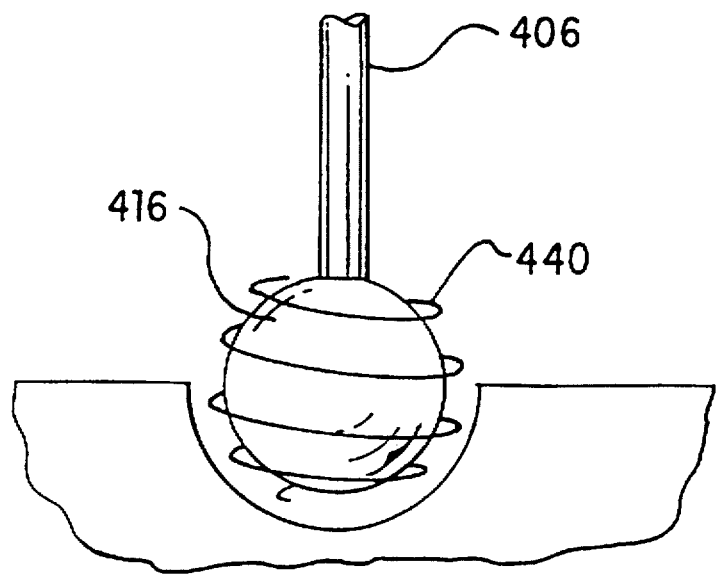
FIG. 9A and FIG. 9B illustrate a deflection of a universal ball joint portion of the bottom of the joystick shaft of FIGS. 7 and 8A.
Figure 9B:
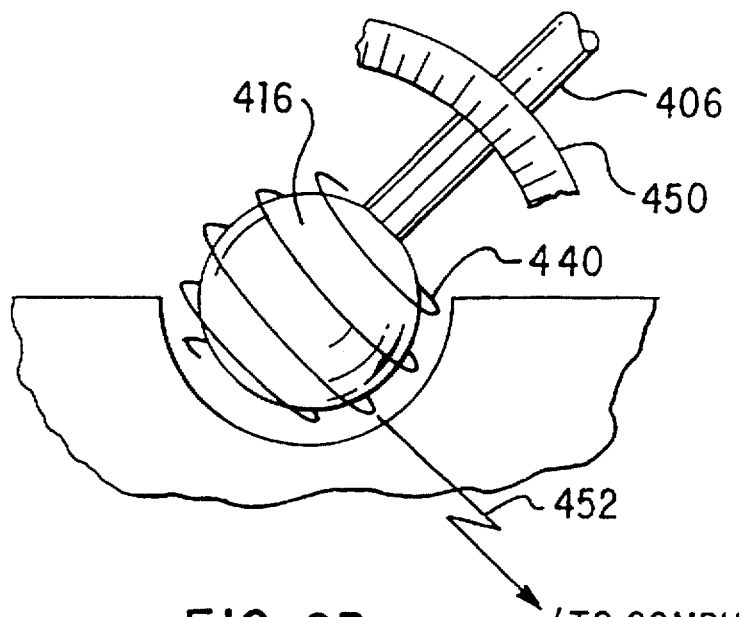

Further features of the joystick devices of FIGS. 7 and 8A and 8B are illustrated in FIGS. 9A and 9B. FIGS. 9A and 9B illustrate the deflection of the rounded portion 416 of the bottom of the joystick and the spring 440 or other device (such as a cam, leaf spring, weighted bottom, magnet, etc.) which is used to return the joystick shaft to the upright neutral position. As illustrated in FIG. 9B, when the shaft 406 is tilted in a certain direction, the spring 440 actually returns the shaft to a neutral position, unless a user is continually applying a force to the handle 402 of the joystick device. Upon deflection of the shaft 406, a device such as gauge 450 may be used to determine the deflection thereof. Alternatively, electrical signal 452 may be provided from the spring to the computer 110 to determine the deflection. Additionally, in order to provide force feedback, a magnet, motor, solenoid, pinchers, constrictors, stepper motors, electromagnetics, cone squeezer, physical constriction along an entire length of the shafts, etc. may be used. The force feedback is provided when the joystick shaft 406 is moved to a point where a collision occurs with the image data stored in the memory of the computer. This is determined, for example, using collision and detection software.

Figure 10:
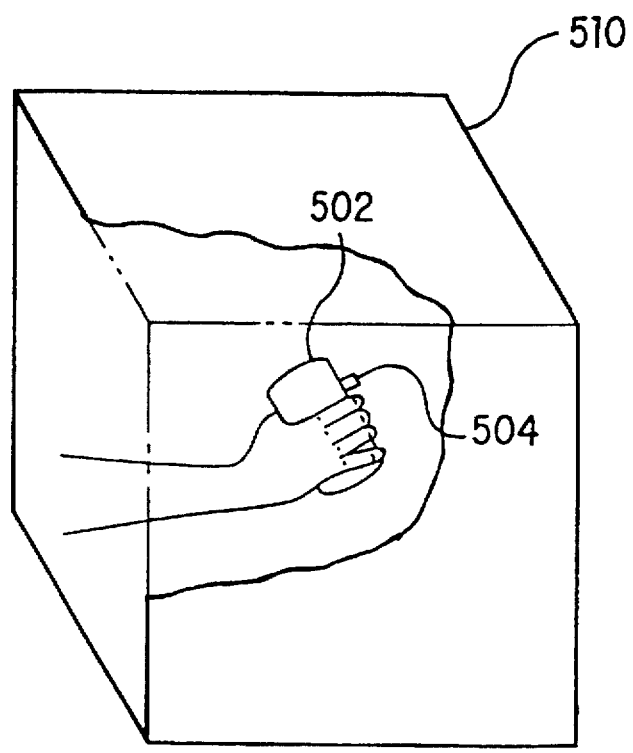
FIG. 10 illustrates a box structure in which a position of a mouse inside the box structure is determined based on laser or ultrasound deflection.

In an alternative embodiment of the present invention illustrated in FIG. 10, a mouse 502 uses lasers or ultrasound emanating from a portion 504 of mouse 502 to detect a position of the mouse based on a deflection of the laser or ultrasound off the walls of a room or box 510 in which the mouse is accommodated. A grid may be provided on the inside walls of box 510 to determine the relative position of the mouse 502 therein. In this manner, three dimensional virtual surgery or other virtual reality may be implemented using a mouse which is freely moveable within the space of the box 510.

In the embodiment of FIG. 10, an array of electric eyes shining at each other, for example, in the left to right and up to down directions within the box or room 510 may be used which shine light at each other to determine a position of the mouse 502 in the box or room 510. Lasers can be used in this embodiment to shine from one side of the box to a photosensor, for example, on the other side of the box in order to scan the space within the box 510 and thereby interpret the reflection of the mouse 502 or transmission to the other side of the box to determine the position of the mouse. Alternatively, ultrasound technology may be used in which proximity sensors are placed on portions of the walls of the box or at opposite sides of the room or outside the box or room to determine a position of the mouse device. Standard mathematical algorithms may be used to determine a position in physical space of the mouse in the room or box in the embodiment of the present invention illustrated in FIG. 10.

Figure 11:
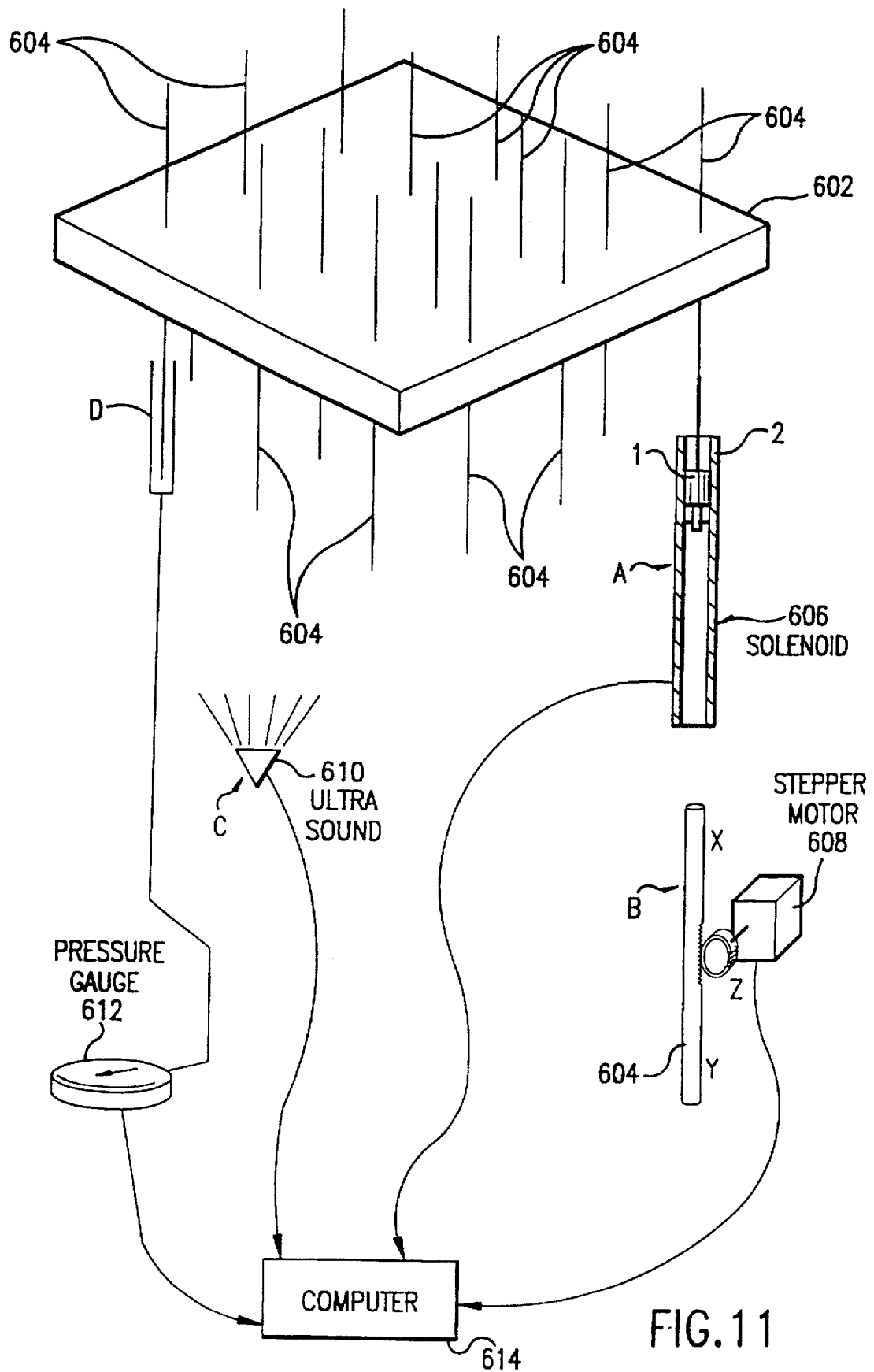
FIG. 11 illustrates a pin input/output device which can input or output digital image information corresponding to output/input physical textures pushed against the pins.

FIG. 11 illustrates a simulated surface input/output device as described below. A plane 602 having a plurality of pins 604 thereon is used for physical modeling and digitization of image data. The pins 604 are of columnar shape with sensors and actuators or solenoids attached to the pins. FIG. 11 shows alternative embodiments in which a solenoid 606, a stepper motor 608, an ultrasound device 610 or a pressure gauge 612 are connected to each of the pins. Any of these devices provide input to a computer 614 via either infrared or connected lines as illustrated in FIG. 11. The pins of FIG. 11 and corresponding solenoid 606, stepper motor 608, ultrasound 610 and pressure gauge 612 operate in the manner as described below.

An input/output device may be used according to an embodiment of the present invention for physical modeling and digitization of image data such as in the embodiment of FIG. 11. The input/output device includes a series of pins 604 of columnar shape with sensors and actuators or solenoids attached to the pins. The pins 604 are arranged in a tight array, either in a single pin depth and a long line or grid with multiple rows in each direction. The pins 604 may be used as an output device by receiving image data from the computer and moving the pins in a position corresponding to the image data values. The pins 604 may be used as an input device by pushing a physical product such as, for example, an artificial hip prosthesis into the pins and recording in the memory of the computer as image data the positioning of the pins based on the physical product being input. This would measure one surface at a time. Each individual pin 604 represents an x and y location in a computerized grid. The z dimension in the grid would be represented by the position of the pin 604 after the device came into contact with the product being recorded. This results in a crude digitization of a simple object or a complex object. No actuating device is required as part of the input device. The device could also detect a position of the pin 604 and move the pin so that each pin 604 is extended out of the surface to a predetermined level based on the digitized model input to the computer. In order to make the texture of the tops of the pins smooth, a surface material can be laid over the pins.

The input/output device of FIG. 11 could be used as an input in a surgical virtual reality system according to an embodiment of the present invention. Additionally, the pin input/output device could be used to input simple or complex shapes for rapid digitizing, including outputting and illustration in Braille text, reproducing maps for the blind, architectural modeling, a medical/physical exam teaching device such as teaching self-examinations to define tumors and superficial body organs (for example, breast or testicle), or modeling of physical appearance for sculpture of forensic medicine.

In a preferred embodiment, the pins 604 of FIG. 11 could be fiber optic in nature. Such an arrangement could facilitate the study of light on three-dimensional objects to allow computer calculation of issues such as the solar gain on a new building or how well an audience might see a performance based on the construction of a stadium.

Additionally, the fiber optic pins would allow the pin array to be very tight. If each of the pins is flexible and enough room was allowed for the advancing and retracking of the pins, the surface of the pins could have an image projected thereon through the fiber optics or by a projector yielding a three-dimensional visual image for a three-dimensional T.V. or a realistic colorized model product. If the material covering the end of the pins is a diffuser of light, the light and image of the overall input physical device could be merged into one so that a clear image can be seen rather than an image including many small points of light.

Figure 12:
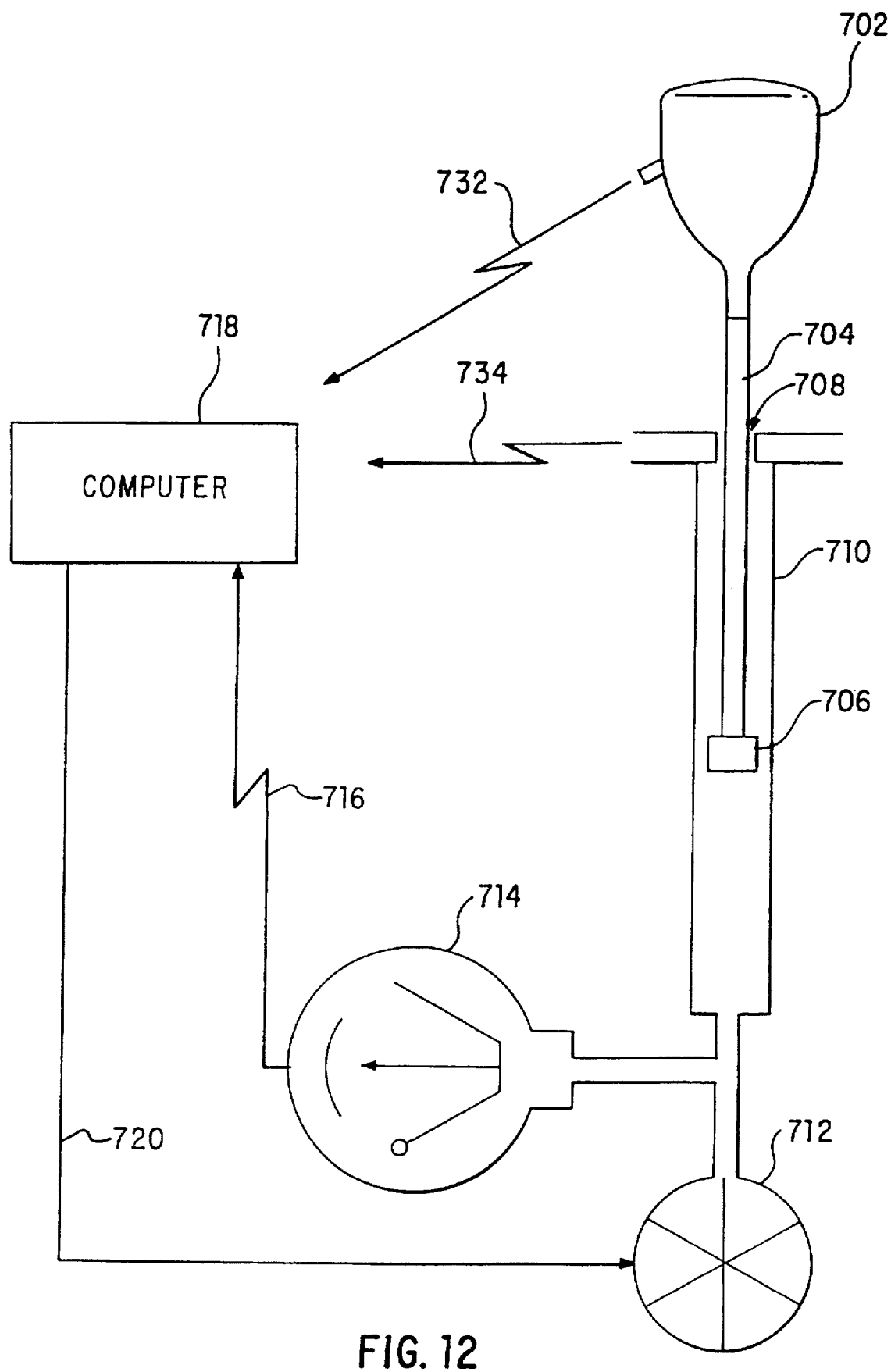
FIG. 12 illustrates a pneumatic or hydraulic feedback device according to an embodiment of the present invention.

FIG. 12 illustrates a pneumatic or hydraulic feedback device for implementing force feedback according to an embodiment of the present invention. The scope handle or mouse device 702 is attached to a shaft 704. A plunger 706 is attached to the bottom of the shaft 704. The shaft 704 protrudes through a virtual orifice 708 and into a housing (or cylinder) 710. A valve wheel with stepper motor control is identified by reference numeral 712. A pressure valve 714 provides a pneumatic feedback signal to computer 718 when an object hit occurs (e.g., when the virtual scope runs into a wall or other portion of the image data). The computer determines an object hit or collision using collision detection software, for example. Upon an object hit, the pressure valve 714 closes and provides the pneumatic feedback signal 716 to computer 718. Computer 718 provides a signal 720 to the valve wheel with stepper motor control 712 to provide the equivalent of a bumpy or rough texture upon turning of the valve wheel 712. This provides force feedback to the plunger 706, shaft 704 and scope handle 702. Infrared signals 732 and 734 are provided to the computer 718 from the scope handle 702 and the virtual orifice 708, respectively.

Force feedback in the embodiment of FIG. 12 is accomplished using a stepper motor with a screw type pneumatic cylinder. The valve wheel can be adjusted based on hydraulics or pneumatics, etc. Forward motion by a user on the scope handle moves the piston or shaft 704 freely. When force is applied, the pressure valve 714 closes on the exit cylinder, thus causing pressure to build against the piston. When a certain force is reached, the piston stops. If the user continues to push on the scope handle, a threshold is reached and "perforation" occurs and pops off a valve release on the pressure valve (not illustrated in FIG. 12). The depth of the plunger (or shaft) into the cylinder 710 corresponds to a similar depth in an organ of the body (e.g., the colon). The force applied by the force feedback provides a similar force as that required for a medical object to advance further into the organ.

Similar resistance to removal can then be accomplished measuring negative pressure. For example, in removing a portion of the anatomy with the scope biopsy instrument, resistance will be met until the tissue pulls away from its initial location.

Figure 13:
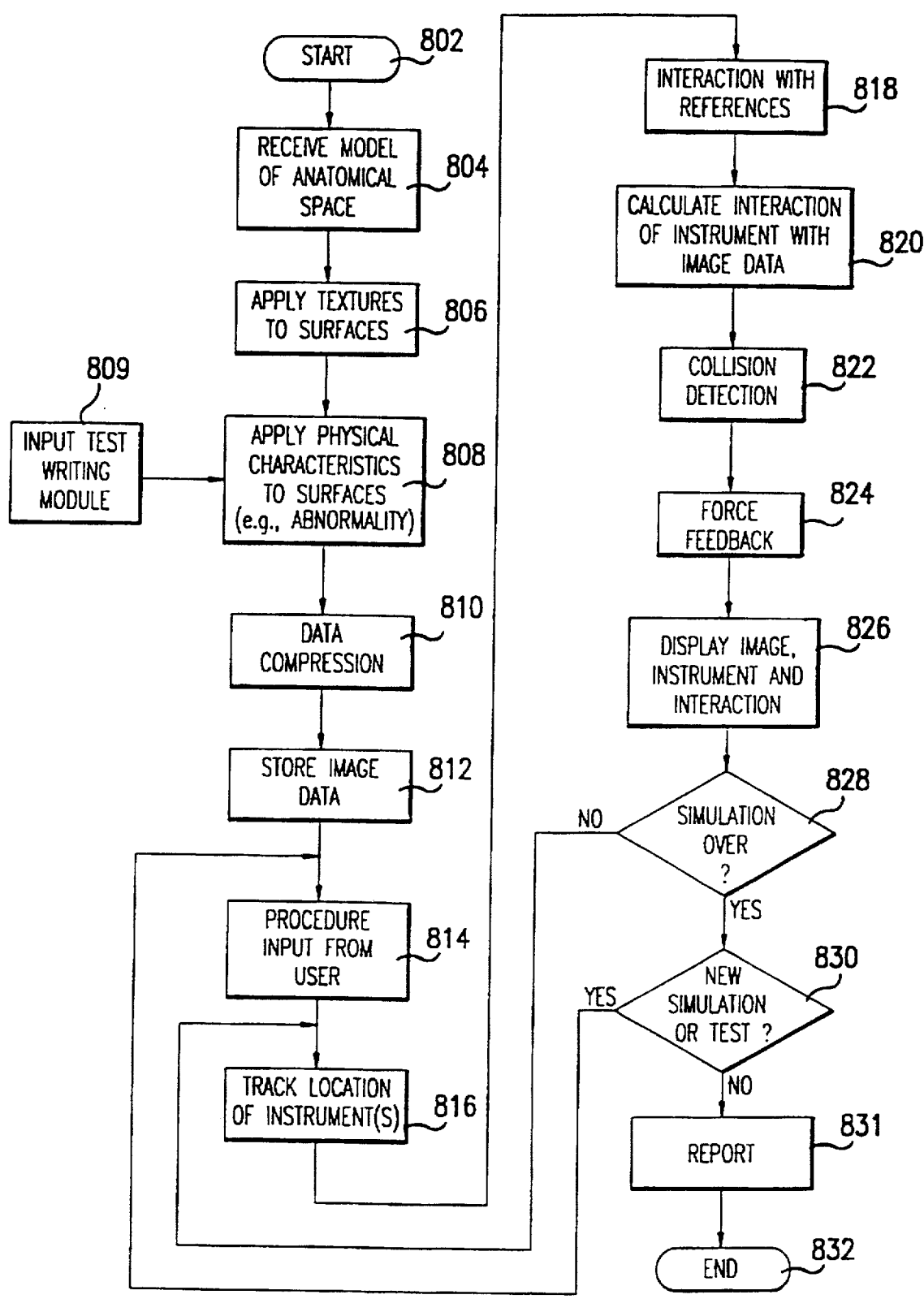
FIG. 13 illustrates a flow chart corresponding to a program implemented in the processor or computer according to an embodiment of the present invention.

FIG. 13 illustrates a flow chart corresponding to a program implemented in a processor or a computer according to an embodiment of the present invention. In particular, a computer program corresponding to the flow chart of FIG. 13 may be implemented by computer 100, processor 102 or computer 718, for example. Further, certain steps of the flow chart of FIG. 13 are optional in a program implemented according to an embodiment of the present invention. Further, additional embodiments of the present invention may be implemented which are not particularly illustrated in the computer flow chart of FIG. 13 as described elsewhere herein.

The programs of the flow chart of FIG. 13 starts at step 802. In step 804, a model of an anatomical space is received by the computer or processor. Textures are applied to visible surfaces of the anatomical space model in step 806. In step 808, physical characteristics are applied to surfaces (e.g., distensibility, elasticity, tensile strength, etc.). As an example, an abnormality may be added to the image data (e.g., image data representing a tumor). A shape, size, proportion, etc. relative to the space in which it is placed may be chosen. Optional step 809 inputs a test writing module. The test writing module allows text questions and task questions to be asked of the test taker. The test taking embodiment is described elsewhere herein, but relates to activity of moving to a location in an anatomy, for example, or performing a required procedure, etc. A Medical Examiner Board, for example, can determine questions to be used based on previous responses or actions by test takers, etc.

Data compression is performed in step 810. This data compression could correspond to averaging, video sequencing or other techniques used to reduce the data load. Alternatively, data compression may not be necessary when medical illustration data or other artist rendition of anatomical image data or other image data are input in the program. A data set of the three dimensional image data space is obtained by the performance of the steps mentioned above. Modifications may be made to the three dimensional image space. Additionally, reference portions may be added to the image space using a training module, a case design module, data corresponding to a test being performed by the virtual surgery system including text or tasks to be performed by the user, or reference to literature references such as medical or other references, on-line medical data, etc. While steps 804–812 are not necessarily performed each time a new simulation is started, these steps may be performed at any time to enter new image data into the computer or new test information or questions.

In step 814, a particular procedure to be used by the user of the virtual surgery system is chosen by a user or a certain test is implemented by the program. A user may pick an anatomical set from the memory, an instrument or instruments to be used by the virtual scope, and other data pertinent to a desired procedure to be implemented. Upon beginning a new procedure in 814, the program of FIG. 13 performs information such as recording information in a personal file corresponding to a particular user, writing multiple text, playback or print to video tape reports corresponding to the virtual surgery to be performed, etc. Step 816 tracks the location of an instrument or instruments being used in the virtual surgery procedure. This tracking of step 816 is performed in response to electronic feedback information from the mouse device, virtual orifice, box, or hose from the virtual surgery system. Step 816, in tracking the location of the instrument or instruments, can determine what the optics at the end of the hose is looking at in the image data, record all movements and locations in the image data, etc. Step 818 performs an optional interaction with reference materials such as, for example, medical texts, files, electronic simulations, other texts, text books, journals, literal searches of journals, still photographs or other digital or non-digital images, motion images, cartoons, other simulations, video, audio (such as a voice announcing location or consultation, either recorded or real-time), references, tests, images, demos, real-time consultation, recorded information, etc. A hypertext linked to references may be made in relation to the location, other text, an abnormality, or a mistake in use of the instrument or judgment of the user. Step 820 calculates the interaction of the virtual instrument with the image data. For example, in a virtual surgery system including more than one virtual scope device (e.g., where a second input device such as biopsy forceps are placed into the scope), image manipulation of the data set may be made through the scope using one or more of the various instruments used in the virtual surgery. The calculating step 820 additionally can monitor an input device such as a keyboard, mouse device, scope device, orifice, joystick, full size instrument, second, third or other plural instruments, a button, switches, a handle, etc.

Step 822 performs edge and collision detection according to standard edge and collision detection software. This edge and collision detection step 822 calculates interaction with surfaces and provides signals corresponding to feedback information such as force feedback. Step 824 performs force feedback to a user in response to the collision detection step 822 using electromechanical, magnetic, etc. devices. Steps 822 and 824 are optional and are not necessary, for example, if a device such as a physical constraint model is used in implementing the present invention.

Step 826 displays the image data, location of the instrument, and any interaction of the instrument with the image data in an area near the current position of the image data. Once a specific location of the anatomy is reached which has been input by the user or required to be found by the user by a test device according to the present invention, text, an image or a request to perform a particular task may be displayed on the display device. This is particularly helpful in the optional examination mode or optional "tour guide" mode, with text, video or image data displayed. Another optional tutor may be used with multimedia demos, for example, from a CDROM or data stored in a memory to tutor a user on how to perform a particular operation either requested by that user or requested by the virtual surgery system.

Steps 828 determines if the simulation has ended. If it has not ended, program flow returns to step 816. If it has ended, step 830 then determines if a new simulation or test procedure is to be performed (either in response to a user input or a requirement of a computer-controlled test, demonstration, etc.). If a new simulation is to be performed, flow returns to step 814. If not, a report is produced in step 831 and step 832 then ends the simulation. The report may relate to a particular experience by the user, a comparison with correct responses, how the simulation may be changed or customized based on overall results, etc.

Figure 14:
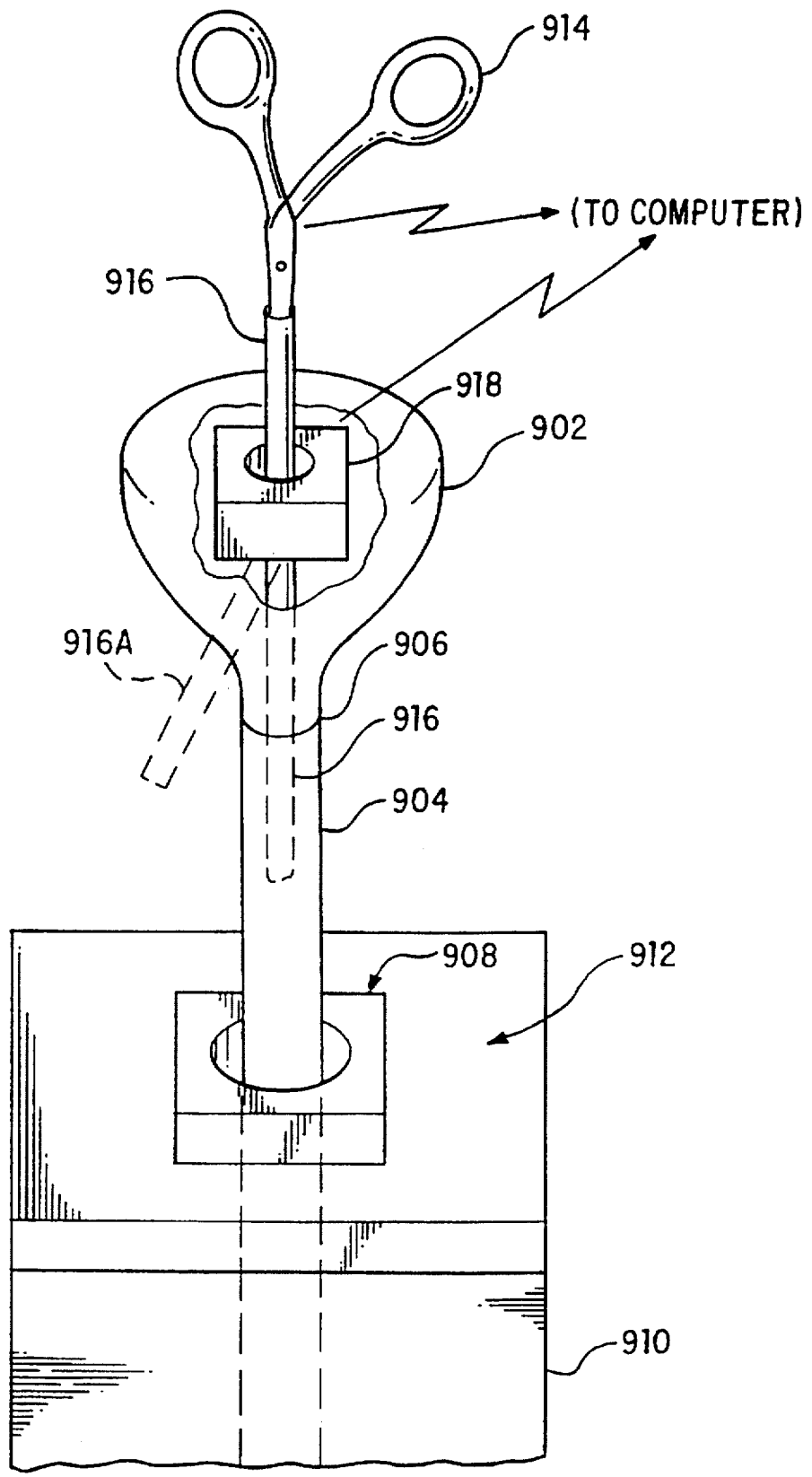
FIG. 14 illustrates an embodiment of the present invention which relates to a "mouse-in-a-mouse", or a "virtual-instrument-in-a-virtual-instrument" or "multiple virtual orifice" implementation of the present invention.

FIG. 14 illustrates an embodiment of the present invention which relates to a "mouse-in-a-mouse", or a "virtual-instrument-in-a-virtual-instrument" or "multiple virtual orifice" implementation of the present invention. A first virtual scope or mouse device 902 is attached to a hose 904 at an end portion 906 thereof. The hose 904 extends through a first virtual orifice 908 and a box device 910. The hose 904 extends into the box device 910 similarly to the hose 108 extending into the box 110 in the embodiment of FIG. 1. A first virtual orifice 908 is attached at a top portion 912 of the box device 910. In the embodiment of FIG. 14, a second instrument 914 such as biopsy forceps is attached to a shaft 916. The shaft 916 extends through a second virtual orifice 918 which is included in the first instrument (or mouse device) 902. Signals from the mouse device 902, the biopsy forceps 914 and/or the first and second virtual orifice 908 and 918, among other locations, is provided to a computer such as computer 100 illustrated in FIG. 1. The shaft 916 extends through the virtual orifice 918 and into the mouse device 902. As illustrated in FIG. 14, the shaft device 916 extends into the hose 904 past the end portion 906 of the mouse device 902. In an alternative embodiment, the shaft 916 could extend into the mouse device 902 through the second virtual orifice 918 without extending into the hose 904, as illustrated by the dotted line shaft 916A.

The biopsy forceps 914 (or other second instrument) included in an embodiment of the present invention as illustrated in FIG. 14 are inserted through a handle of the first virtual scope 902 through the simulated second orifice 918 of the scope 902. In a preferred embodiment, the virtual shaft 916 is extended through the virtual scope 902. The device could have a handle on either mouse device 902 or biopsy forceps 914, for example, to simulate cutting, biopsying, laser work, or other activity. As discussed above, the shaft 916 can exit through the handle or a hollow channel in the shaft of the scope, or into the hose 904. This allows a simulation of a multiple instrument surgical procedure used by an operator through the simulated scope and first and second orifices. Force feedback may also be performed according to the above discussion.

Biopsy forceps 914 could alternatively be replaced by a syringe handle, scissors, or other instrument appropriate for a particular operation. As mentioned above, the embodiment of FIG. 14 provides a scope within a scope or mouse within a mouse implementation of virtual surgery according to an embodiment of the present invention. Shaft 916 operates as the working handle and provides operational switching electronically hooked to the computer (not illustrated in FIG. 14).

In implementing the multiple virtual scope device illustrated in FIG. 14, a user can manipulate the first virtual scope 902 through the first virtual orifice 908 to get to a particular location. The second virtual scope (or biopsy forceps) 914 is then added via shaft 916 for cutting, biopsy, laser, or other work to be performed in a virtual operation. Manipulation of the biopsy forceps 914 moves both of the virtual orifices illustrated in FIG. 14. In this manner, the multiple mouse or virtual scope embodiment simulates a standard endoscopic biopsy technique or other use of multiple tools in a channel of a scope to provide virtual scope within a scope or mouse within a mouse simulation.

Figure 15:
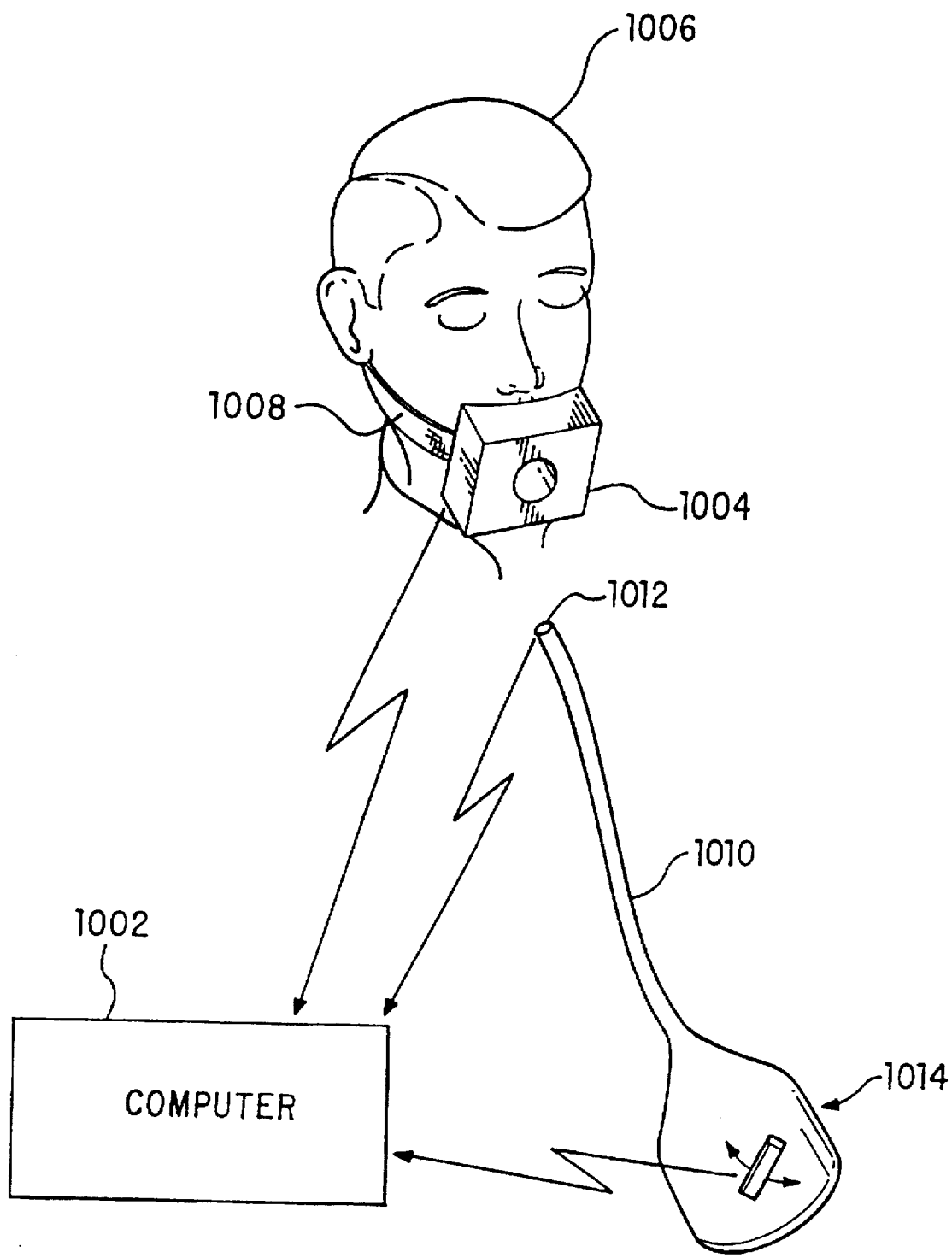
FIG. 15 illustrates a real surgery implementation of the present invention at a mouth orifice of a patient.

FIG. 15 illustrates a real surgery implementation of the present invention at a mouth orifice of a patient. FIG. 15 illustrates an embodiment of the present invention in which actual surgery data may be obtained by a computer 1002. A virtual orifice 1004 is attached over a real orifice of a patient 1006 (in the embodiment of FIG. 15, the real orifice is the patient's mouth). The virtual orifice 1004 is attached to the patient 1006 using a device to hold the virtual orifice 1004 in place, such as cloth ties 1008. A real endoscope 1010 is then used by a surgeon to perform real surgery on the patient 1006. The endoscope is placed through the virtual orifice 1004 and into the patient's mouth to perform the real surgery. The motion of the endoscope 1010 within the patient's mouth is tracked by the computer 1002, which receives signals from the virtual orifice 1004, the end 1012 of the real endoscope 1010, the handle 1014 of the real endoscope 1010, etc. For example, the sequence and time in each region of the anatomy may be recorded and/or the anatomy may be re-created. The motion during the real surgery tracked using this embodiment may be merged with CT scan data or other three dimensional data, merged with images from the scope, or merged with any other image data. Alternatively, a simulation may be merged with real video, pictures or image data obtained during the real surgical procedure (e.g., from the real endoscope or virtual orifice). This creates a marked improvement in documenting an actual procedure for a patient's medical record. This data may be stored in a memory of the computer 1002, or in any other recording device such as a CDROM, magnetic tape, computer disc, etc. The saved data may be used to re-create an actual surgery (e.g., in forensic medicine, in legal courtroom for medical malpractice purposes, for teaching purposes, or for review of a surgeon's work by the surgeon's superiors, the surgeon's peers and/or a Medical Review Board or Medical Examination Board, etc.). Further, the computer may take the stored data tracking the motion of the surgery, either alone or with the merged ultrasound scan, CT scan, MRI scan, PET scan, etc. and provide the information to a recording device (video tape, CDROM, etc.). The recording device may then be forwarded to a virtual surgery system such as in the embodiment of FIG. 1 (e.g., via courier or U.S. Postal Service) to be used as an instructional device, for example. The image data may also be provided electronically via Internet, modem, etc. to a virtual surgery system according to an embodiment of the present invention.

In a virtual surgery system according to the present invention as described above, as a user moves a virtual scope to traverse through an image space and perform virtual surgery in that image space, the computer or processor tracks where the endoscopic camera is, and what that camera is looking at. In this manner, the position of the virtual scope arrangement and objects caught by the camera image in the image space are determined by the computer. The virtual surgery system according to the present invention may be used as a simulator including testing, test altering, test taking, assessment, training, etc. purposes. A user could go to the virtual surgery system and chose a particular virtual surgery to be performed, or alternatively could enter a demonstration mode or testing, etc. mode. In a mode in which the computer acts as a tutor or "tour guide", the user may be asked certain questions by the virtual surgery system, either by a question displayed on the display device or even a question posed to the user through, for example, a speech synthesis device. The virtual surgery system can tell the pupil or test taker where the virtual scope or input device is located at in a portion of the anatomy or can ask the test taker questions or require the test taker to traverse through the image space to a particular portion of the anatomy or perform a particular surgical operation on a portion of the anatomy. The tutor device can also require the user to perform a particular surgery or other procedure to a certain portion of the anatomy and can give feedback relating to the user's performance. For example, the virtual surgery system could tell the user that the device is in a particular portion of the anatomy or give the user instructions on how to get to a particular portion of the anatomy. Feedback result data may be provided to a pupil, user, or test taker via audio, video or text on the display screen. A text box, audio file or video file may be used in which a demonstration is performed by the simulator showing the student how to perform the particular required operation. The simulator can show a user how to perform the operation correctly or a picture of an image of the portion of the anatomy to which the user is attempting to locate using the simulator.

An inexperienced doctor or student could use the tour guide before performing a new procedure, then practice the procedure using the simulator, and eventually perform the real procedure (e.g., a real surgery on a patient or other real procedure). Additionally, the doctor's or student's simulation could be stored in the computer for later review by the doctor's or student's superiors and/or teachers, etc.

The virtual surgery system of the present invention may also be used in relation to teleradiology, telesurgery, telemedicine, telemonitoring, etc. Teleradiology digitizes and provides image data for a particular patient. This digitized and imaged data can be used as an input to the virtual surgery system and stored in the memory of the computer, for example. The medical information or image data can also be provided to the virtual surgery device via a modem, telephone, satellite, etc. connection providing analog or digital data to be stored in the virtual surgery system for later use. Additionally, patient monitoring information can be stored in the virtual surgery system for later use in virtual surgery.

Telesurgery may be used according to an embodiment of the present invention in order for a surgeon to perform surgery from a distance, or to provide consultation to another surgeon performing a real operation by an expert surgeon watching the real operation and instructing the doctor using a simulation of a similar operation, etc. In an application in which a surgeon performs surgery at a remote location, a robot can be used to simulate hand movements of the surgeon at the remote location via a tele-robotic unit. The robot can move the real endoscope or other surgical device according to the movements of the surgeon performed using a virtual scope. In another embodiment of the present invention, a surgical procedure can be simulated by an expert surgeon, for example, in a library tutorial provided on a video tape, CDROM, electronic device such as a modem, etc. Alternatively, the simulated procedure can be provided by one surgeon to another surgeon at a remote location in real-time using a video data feed. For example, a surgeon using a real endoscope looking at a real patient and moving the endoscope inside the orifices of a real patient, can receive video corresponding to data transmitted electronically to a remote point (e.g., from the Mayo Clinic or via the Internet), and an expert watching the operation in real-time can show the actual doctor performing the real surgery a simulation of the operation or provide particular guidance to the other surgeon performing the real operation. This guidance can be provided on a display screen in the actual operating room while the surgeon is operating on the actual patient.

A storage library can be implemented according to an embodiment of the present invention in which a library of image data simulations, problems encountered, etc. are stored for later retrieval by a student or surgeon. For example, an expert surgeon holding a simulator can simulate a biopsy or how to use a laser or particular surgical device on a patient with a particular abnormality or operation to be performed. The simulation library can also include particular image data corresponding to a specific patient. Such image data corresponding to a patient can be stored as a part of that patient's medical record, for example.

The present invention can also be used in a tele-robotics application for other implementations other than virtual surgery. For example, a virtual industrial application or other virtual procedure can be implemented according to an embodiment of the present invention.

Force feedback may be performed in implementing the present invention described herein using a spinning stepper motor, pressure, pinchers, constrictors, electromagnetics (e.g., when the scope is coated with a magnetic material and a magnet is used to create friction or resistance to the scope), or variable tension using electromagnetics, pneumatics, hydraulics, etc., or other electronics such as solenoids, etc. A constriction device which may be used according to an embodiment of the present invention for force feedback which uses cone-shaped squeezers to simulate constriction of the scope. Alternatively physical constriction can be provided along an entire length of the simulator.

A virtual surgery system according to an embodiment of the present invention can be used in which an input device is used by a user to perform virtual surgery or virtual medical testing or virtual testing of other industrial applications as described above. The input device used in implementing the present invention has been described herein as being a mouse device, a seven dimensional joystick device, a full size simulator, etc. The input device used according to embodiments of the present invention can include a keyboard, a standard mouse, a three dimensional mouse, a standard joystick, a seven dimensional joystick, or a full size simulator with a full size mock-up of a medical or other industrial type instrument. Additionally, any of these input devices can be used in the present invention with force feedback being performed. Physical force feedback can be implemented using physical constraint models or edge and collision detection software techniques.

Other embodiments of the present invention can be used in which, for example, a patient has image data scanned into the system, and during a simulation or a real surgery operation, a portion of the display screen shows a pre-recorded expert simulation via video tape, CDROM, etc., or a real-time tutorial by another doctor. Telesurgery applications may also be used as described above, in which a surgeon moves an input device (e.g., a full-size virtual scope or instrument) of a simulator while a robot actually performs a real operation based on the simulated motions of a surgeon at a remote location. The present invention may be used in a testing embodiment in which the virtual surgery device or other testing device questions via text and specific task questions. For example, in a medical embodiment, the virtual device might ask a test taker to go to a particular location in the anatomy and then perform a biopsy. Questions may be inserted in the test before, during or after a particular operation (such as a bronchoscopy). A multitude of tasks may be required of a student during the test procedure. The test taker may chose between different modes, such as an illustration, practice or exam mode. As a result of students tests, reports may be issued relating to the experience a particular student had during the test, how well they did, in comparison to the correct procedures with the individuals performance, and an indication of the performance of all individuals taking these tests for a particular question. In this manner, an exam can be determined and customized for a particular company, for example. In another embodiment, the Medical Examination Board can identify different test questions by case, one time individual performance, cumulative performance by an individual, etc., and can provide different levels of difficulty. The virtual surgery system of the present invention or other test taking device not related to surgery or medical applications can include training, test taking and records archiving abilities (for example, in a medical context this archiving can relate to a patient's medical records).

In a medicine simulation embodiment of the present invention, volumes, surfaces of volumes, various characteristics and images of surfaces may be merged with real images or illustrated images using mathematical algorithms. Algorithms may also be used to determine the intersection of surfaces in the image set with the particular test taking device. Simulation through the image data may be made while saving documentation, questions and other information relating to the manipulation of the image volumes. In another embodiment of the present invention, multimedia demonstrations may obtained from the manufacturer of a particular instrument or a manufacturer of an instrument different from the instrument being used. If a surgeon or other user is using a new instrument, a demonstration may be made at the time of use (for example, in an operating room), without even using a simulating device. The surgeon or other user could then use the new real instrument in response to touching the touch screen on the simulator device, for example. In this manner a reference file is accessible at a point of use. In another embodiment, the touch screen of the simulator can be used to get on-line help from a manufacturer, medical director, etc., or an order for such help or a particular product may be made immediately using the touch screen. References, experts, catalogs, products, demonstrations on how to use the product, etc. could be referred to either in real-time, using prerecorded messages or ordering commands via the simulating device or other device such as a touch screen.

What is claimed is:

1. A telesurgery device, comprising:
    a user input device, wherein said user input device includes a surgical instrument simulator and a housing wherein said surgical instrument simulator physically simulates an actual surgical instrument and said housing includes a virtual orifice, said surgical instrument simulator being partially received within said housing through said virtual orifice;
    a memory storing non-real time data associated with a patient;
    means for simulating a surgical procedure, wherein said means for simulating a surgical procedure is located remote from the patient and wherein said means for simulating a surgical procedure simulates a surgical procedure by utilizing data received from said user input device and said non-real time data associated with the patient stored in said memory;
    a robot having a surgical tool for performing an actual surgical procedure on the patient; and
    a transmission device connecting said means for simulating a surgical procedure to said robot, said robot performing an actual surgical procedure on the patient in response to the simulated surgical procedure.

2. The telesurgery device according to claim 1 wherein said means for simulating a surgical procedure transmits data for simulating a surgical procedure directly to said user input device.

3. The telesurgery device according to claim 2 wherein said data for simulating a surgical procedure transmitted to said user input device is force feedback.

4. The telesurgery device according to claim 1 wherein said virtual orifice is connected to said means for simulating a surgical procedure and wherein data for simulating a surgical procedure is transmitted bi-directionally between said virtual orifice and said means for simulating a surgical procedure.

5. The telesurgery device according to claim 1 wherein said non-real time data associated with a patient is image data of the anatomy of the patient.

6. The telesurgery device according to claim 1 wherein said non-real time data associated with a patient is historical medical information of the patient.

7. A telesurgery device, comprising:
    a user input device, said user input device including a surgical instrument simulator and a housing having a virtual orifice wherein said surgical instrument simulator is partially received within said housing through said virtual orifice;
    a computer for simulating a surgical procedure, said computer located remote from an actual patient and having memory storing non-real time image data of the actual patient wherein said computer receives data for simulating a surgical procedure from said surgical instrument simulator, said housing, and said virtual orifice and wherein said computer directly transmits data for simulating a surgical procedure to said surgical instrument simulator, said housing, and said virtual orifice;
    said computer simulating a surgical procedure by utilizing data received from and transmitted to said user input device and said non-real time image data associated with the patient stored in said memory;
    a robot having a surgical tool for performing an actual surgical procedure on the patient; and
    a transmission device connecting said computer to said robot, said robot performing an actual surgical procedure on the patient in response to the simulated surgical procedure.

8. The telesurgery device according to claim 7 wherein said stored non-real time image data of an actual patient is data obtained from a computerized axial tomography scan.

9. The telesurgery device according to claim 7 wherein said stored non-real time image data of an actual patient is data obtained from a magnetic resonance imager.

10. A method for performing a telesurgery operation comprising the steps of:
    storing non-real time data of an actual patient in memory of a computer;
    performing a simulated surgical procedure by utilizing said stored non-real time data of the actual patient and a user input device wherein said user input device includes a surgical instrument simulator and a housing, wherein said surgical instrument simulator physically simulates an actual surgical instrument and said housing includes a virtual orifice and wherein said surgical instrument simulator is partially received within said housing through said virtual orifice;
    transmitting the movements of said user input device to a location remote from the location where the simulated surgical procedure is performed;
    receiving the movements of said user input device at a location remote from the location where the simulated surgical procedure is performed;
    controlling the movements of a robot by said received movements of said user input device; and
    performing an actual surgical procedure by said robot, said actual surgical procedure performed by said robot in response to said movements of said user input device.

11. The method for performing a telesurgery operation according to claim 10 further comprising the step of receiving real time data from the patient and wherein said step of performing a simulated surgical procedure utilizes said real time data received from the patient.

12. The method for performing a telesurgery operation according to claim 10 wherein said virtual orifice is connected to a computer for simulating a surgical procedure and wherein said virtual orifice transmits data to said computer and receives data from said computer.

13. The method for performing a telesurgery operation according to claim 11 wherein said real time data received from the patient is merged with said stored non-real time data of the actual patient and wherein said step of performing a simulated surgical procedure utilizes said merged data.

14. The telesurgery device according to claim 1 wherein said means for simulating a surgical procedure simulates a surgical procedure by utilizing real time data received from the patient merged with said non-real time data associated with the patient.

15. The telesurgery device according to claim 7 wherein said computer simulates a surgical procedure by utilizing real time image data received from the patient merged with said non-real time image data associated with the patient.

16. The method for performing a telesurgery operation according to claim 10 wherein said computer is a personal computer and wherein said non-real time data of the actual patient is acquired from a super computer and downloaded from the super computer to said personal computer.

17. The telesurgery device according to claim 7 wherein said computer is a personal computer and wherein said non-real time image data of the actual patient is acquired from a super computer and downloaded from the super computer to said personal computer.

18. The method for performing a telesurgery operation according to claim 10 further comprising the steps of:

transmitting said stored non-real time data of the actual patient to a surgeon at a second remote location, said second remote location being remote from the location where the simulated surgical procedure is performed and remote from the location where the actual surgical procedure is performed;

receiving said stored non-real time data of the actual patient at said second remote location;

analyzing said stored non-real time data at said second remote location:

transmitting data representative of said analysis of said stored non-real time data to said location where the simulated procedure is performed: and receiving said data representative of said analysis of said stored non-real time data at said location where the simulated procedure is performed:

wherein said step of performing a simulated surgical procedure is performed by utilizing said stored non-real time data of the actual patient, said user input device and said data received from said second remote location.

* * * * *